(12) United States Patent
Kao et al.

(10) Patent No.: US 8,282,680 B2
(45) Date of Patent: Oct. 9, 2012

(54) MULTIPLE INDEPENDENT NESTED STENT STRUCTURES AND METHODS FOR THEIR PREPARATION AND DEPLOYMENT

(75) Inventors: Stephen Kao, Mountain View, CA (US); Bernard Andreas, Redwood City, CA (US); Hanson S. Gifford, III, Woodside, CA (US); Mark E. Deem, Mountain View, CA (US); David W. Snow, Menlo Park, CA (US); Jeffry J. Grainger, Portola Valley, CA (US)

(73) Assignee: J. W. Medical Systems Ltd., Weihai Shandong (CN)

( * ) Notice: Subject to any disclaimer, the term of this patent is extended or adjusted under 35 U.S.C. 154(b) by 0 days.

(21) Appl. No.: 12/492,828

(22) Filed: Jun. 26, 2009

(65) Prior Publication Data

US 2009/0264979 A1 Oct. 22, 2009

Related U.S. Application Data

(63) Continuation of application No. 10/738,666, filed on Dec. 16, 2003, now abandoned.

(60) Provisional application No. 60/440,839, filed on Jan. 17, 2003.

(51) Int. Cl.
*A61F 2/06* (2006.01)
(52) U.S. Cl. ............................................ 623/1.16
(58) Field of Classification Search ................. 623/1.15, 623/1.16, 1.11, 1.42–1.48, 1.12, 1.2; 606/194; 604/101.01, 101.05
See application file for complete search history.

(56) References Cited

U.S. PATENT DOCUMENTS

| 4,069,825 A | 1/1978 | Akiyama |
| 4,468,224 A | 8/1984 | Enzmann et al. |
| 4,512,338 A | 4/1985 | Balko et al. |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |

(Continued)

FOREIGN PATENT DOCUMENTS

DE 1 953 1659 3/1997

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner* — Kathleen Sonnett
*Assistant Examiner* — Jocelin Tanner
(74) *Attorney, Agent, or Firm* — Kilpatrick Townsend & Stockton LLP

(57) ABSTRACT

Blood vessels and other body lumens are stented using stent structures comprising a plurality of radially expansible rings where at least some of the rings comprise axially extending elements which interleave with axially extending elements on adjacent unconnected rings. The ring structures may be open cell structures or closed cell structures, and the axially extending elements will typically be formed as part of the open cell or closed cell structure.

66 Claims, 22 Drawing Sheets

U.S. PATENT DOCUMENTS

| | | | |
|---|---|---|---|
| 4,770,176 A | 9/1988 | McGreevy et al. | |
| 4,775,337 A | 10/1988 | Van Wagener et al. | |
| 4,776,337 A | 10/1988 | Palmaz | |
| 4,886,062 A | 12/1989 | Wiktor | |
| 4,891,225 A | 1/1990 | Langer et al. | |
| 4,950,227 A | 8/1990 | Savin et al. | |
| 4,988,356 A | 1/1991 | Crittenden et al. | |
| 4,994,066 A | 2/1991 | Voss | |
| 4,994,069 A | 2/1991 | Ritchart et al. | |
| 4,994,298 A | 2/1991 | Yasuda | |
| 5,013,318 A | 5/1991 | Spranza, III | |
| 5,035,706 A | 7/1991 | Giantureo et al. | |
| 5,040,548 A | 8/1991 | Yock | |
| 5,061,273 A | 10/1991 | Yock | |
| 5,064,435 A | 11/1991 | Porter | |
| 5,092,877 A | 3/1992 | Pinchuk | |
| 5,102,417 A | 4/1992 | Palmaz | |
| 5,104,404 A | 4/1992 | Wolff | |
| 5,122,154 A | 6/1992 | Rhodes | |
| 5,135,535 A | 8/1992 | Kramer | |
| 5,158,548 A | 10/1992 | Lau et al. | |
| 5,192,297 A | 3/1993 | Hull | |
| 5,195,984 A | 3/1993 | Schatz | |
| 5,201,757 A | 4/1993 | Heyn et al. | |
| 5,217,495 A | 6/1993 | Kaplan et al. | |
| 5,219,355 A | 6/1993 | Parodi et al. | |
| 5,226,913 A | 7/1993 | Pinchuk | |
| 5,246,421 A | 9/1993 | Saab | |
| 5,273,536 A | 12/1993 | Savas | |
| 5,282,824 A | 2/1994 | Gianturco | |
| 5,300,085 A | 4/1994 | Yock | |
| 5,312,415 A | 5/1994 | Palermo | |
| 5,334,187 A | 8/1994 | Fischell et al. | |
| 5,391,172 A | 2/1995 | Williams et al. | |
| 5,421,955 A | 6/1995 | Lau et al. | |
| 5,443,498 A | 8/1995 | Fontaine | |
| 5,445,646 A | 8/1995 | Euteneuer et al. | |
| 5,456,713 A | 10/1995 | Chuter | |
| 5,458,615 A | 10/1995 | Klemm et al. | |
| 5,470,315 A | 11/1995 | Adams | |
| 5,478,349 A | 12/1995 | Nicholas | |
| 5,490,837 A | 2/1996 | Blaeser et al. | |
| 5,496,346 A | 3/1996 | Horzewski et al. | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,527,354 A | 6/1996 | Fontaine et al. | |
| 5,531,735 A | 7/1996 | Thompson | |
| 5,533,968 A | 7/1996 | Muni et al. | |
| 5,534,007 A | 7/1996 | St. Germain et al. | |
| 5,545,209 A | 8/1996 | Roberts et al. | |
| 5,549,551 A | 8/1996 | Peacock, III et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,571,086 A | 11/1996 | Kaplan et al. | |
| 5,591,195 A | 1/1997 | Taheri et al. | |
| 5,593,412 A | 1/1997 | Martinez et al. | |
| 5,607,444 A | 3/1997 | Lam | |
| 5,607,463 A | 3/1997 | Schwartz et al. | |
| 5,628,755 A | 5/1997 | Heller et al. | |
| 5,628,775 A | 5/1997 | Jackson et al. | |
| 5,634,928 A | 6/1997 | Fischell et al. | |
| 5,639,274 A | 6/1997 | Fischell et al. | |
| 5,662,675 A | 9/1997 | Polanskyj Stockert et al. | |
| 5,670,161 A | 9/1997 | Healy et al. | |
| 5,676,654 A | 10/1997 | Ellis et al. | |
| 5,683,451 A | 11/1997 | Lenker et al. | |
| 5,690,644 A | 11/1997 | Yurek et al. | |
| 5,693,085 A | 12/1997 | Buirge et al. | |
| 5,697,948 A | 12/1997 | Marin et al. | |
| 5,697,971 A | 12/1997 | Fischell et al. | |
| 5,702,418 A | 12/1997 | Ravenscroft | |
| 5,709,701 A | 1/1998 | Parodi | |
| 5,716,393 A | 2/1998 | Lindenberg et al. | |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,741,323 A | 4/1998 | Pathak et al. | |
| 5,749,848 A | 5/1998 | Jang et al. | |
| 5,749,921 A | 5/1998 | Lenker et al. | |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,792,144 A | 8/1998 | Fischell et al. | |
| 5,797,951 A | 8/1998 | Mueller | |
| 5,800,519 A | 9/1998 | Sandock | |
| 5,807,398 A | 9/1998 | Shaknovich | |
| 5,824,040 A | 10/1998 | Cox et al. | |
| 5,824,041 A | 10/1998 | Lenker et al. | |
| 5,833,694 A * | 11/1998 | Poncet | 623/1.11 |
| 5,836,964 A | 11/1998 | Richter et al. | |
| 5,843,092 A | 12/1998 | Heller et al. | |
| 5,855,563 A | 1/1999 | Kaplan et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,899,935 A | 5/1999 | Ding | |
| 5,902,332 A | 5/1999 | Schatz | |
| 5,919,175 A | 7/1999 | Sirhan | |
| 5,921,971 A | 7/1999 | Agro et al. | |
| 5,922,020 A | 7/1999 | Klein et al. | |
| 5,941,869 A | 8/1999 | Patterson et al. | |
| 5,951,585 A | 9/1999 | Cathcart et al. | |
| 5,961,536 A | 10/1999 | Mickley et al. | |
| 5,968,069 A | 10/1999 | Dusbabek et al. | |
| 5,972,027 A | 10/1999 | Johnson | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 5,989,280 A | 11/1999 | Euteneuer et al. | |
| 5,993,484 A | 11/1999 | Shmulewitz | |
| 5,997,563 A | 12/1999 | Kretzers | |
| 6,004,328 A | 12/1999 | Solar | |
| 6,007,517 A | 12/1999 | Anderson | |
| 6,010,530 A | 1/2000 | Goicoechea | |
| 6,022,359 A | 2/2000 | Frantzen | |
| 6,022,374 A | 2/2000 | Imran | |
| 6,027,519 A | 2/2000 | Stanford | |
| 6,033,434 A | 3/2000 | Borghi | |
| 6,036,725 A | 3/2000 | Avellanet | |
| 6,039,721 A | 3/2000 | Johnson et al. | |
| 6,042,589 A | 3/2000 | Marianne | |
| 6,056,722 A | 5/2000 | Jayaraman | |
| 6,063,111 A | 5/2000 | Hieshima et al. | |
| 6,066,155 A | 5/2000 | Amann et al. | |
| 6,068,655 A | 5/2000 | Seguin et al. | |
| 6,070,589 A | 6/2000 | Keith et al. | |
| 6,090,063 A | 7/2000 | Makower et al. | |
| 6,090,136 A | 7/2000 | McDonald et al. | |
| 6,102,942 A | 8/2000 | Ahari | |
| 6,106,530 A | 8/2000 | Harada | |
| RE36,857 E | 9/2000 | Euteneuer et al. | |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler et al. | |
| 6,132,460 A | 10/2000 | Thompson | |
| 6,139,572 A | 10/2000 | Campbell et al. | |
| 6,143,016 A | 11/2000 | Bleam et al. | |
| 6,165,167 A | 12/2000 | Delaloye | |
| 6,165,210 A | 12/2000 | Lau et al. | |
| 6,171,334 B1 | 1/2001 | Cox | |
| 6,179,878 B1 | 1/2001 | Duerig et al. | |

| | | |
|---|---|---|
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,409,753 B1 | 6/2002 | Brown et al. |
| 6,415,696 B1 | 7/2002 | Erickson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 * | 8/2004 | van Moorlegem et al. ........ 604/101.01 |
| 6,778,316 B2 | 8/2004 | Halas et al. |
| 6,790,227 B2 | 9/2004 | Burgermeister |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,913,619 B2 | 7/2005 | Brown et al. |
| 6,918,928 B2 | 7/2005 | Wolinsky et al. |
| 6,939,376 B2 | 9/2005 | Shulze et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,005,454 B2 | 2/2006 | Brocchini et al. |
| 7,022,132 B2 | 4/2006 | Kocur |
| 7,029,493 B2 * | 4/2006 | Majercak et al. ............ 623/1.15 |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |
| 7,241,308 B2 | 7/2007 | Andreas et al. |
| 7,244,336 B2 | 7/2007 | Andreas et al. |
| 7,270,668 B2 | 9/2007 | Andreas et al. |
| 7,294,146 B2 | 11/2007 | Chew et al. |
| 7,300,456 B2 | 11/2007 | Andreas et al. |

| | | |
|---|---|---|
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,918,881 B2 | 4/2011 | Andreas et al. |
| 7,993,388 B2 | 8/2011 | Lee et al. |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2002/0007212 A1 | 1/2002 | Brown et al. |
| 2002/0035395 A1* | 3/2002 | Sugimoto .................. 623/1.15 |
| 2002/0037358 A1 | 3/2002 | Barry et al. |
| 2002/0052642 A1 | 5/2002 | Cox et al. |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0128706 A1 | 9/2002 | Osypka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1* | 10/2002 | Chermoni .................. 606/194 |
| 2002/0165599 A1* | 11/2002 | Nasralla .................. 623/1.11 |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1* | 5/2003 | Zhao et al. ............. 623/1.15 |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0106979 A1 | 6/2004 | Goicoechea et al. |
| 2004/0111145 A1 | 6/2004 | Serino et al. |
| 2004/0117008 A1 | 6/2004 | Wnendt et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1* | 12/2004 | Andersen et al. ............. 623/1.15 |
| 2004/0249434 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0080474 A1 | 4/2005 | Andreas et al. |
| 2005/0080475 A1 | 4/2005 | Andreas et al. |
| 2005/0090846 A1 | 4/2005 | Pedersen et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0137622 A1 | 6/2005 | Griffin |
| 2005/0143827 A1 | 6/2005 | Globerman et al. |
| 2005/0149168 A1 | 7/2005 | Gregorich |
| 2005/0165378 A1 | 7/2005 | Heinrich et al. |
| 2005/0182477 A1* | 8/2005 | White ..................... 623/1.15 |
| 2005/0209674 A1 | 9/2005 | Kutscher et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0125850 A1 | 5/2008 | Andreas |
| 2008/0132989 A1 | 6/2008 | Snow et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |

| | | | |
|---|---|---|---|
| 2008/0234798 A1 | 9/2008 | Chew et al. | |
| 2008/0234799 A1 | 9/2008 | Acosta et al. | |
| 2008/0243225 A1 | 10/2008 | Satasiya et al. | |
| 2008/0249607 A1 | 10/2008 | Webster et al. | |
| 2008/0269865 A1 | 10/2008 | Snow et al. | |
| 2009/0076584 A1 | 3/2009 | Mao et al. | |
| 2009/0105686 A1 | 4/2009 | Snow et al. | |
| 2009/0149863 A1 | 6/2009 | Andreas et al. | |
| 2009/0234428 A1 | 9/2009 | Snow et al. | |
| 2009/0248137 A1 | 10/2009 | Andersen et al. | |
| 2009/0248140 A1 | 10/2009 | Gerberding | |
| 2010/0004729 A1 | 1/2010 | Chew et al. | |

FOREIGN PATENT DOCUMENTS

| | | | |
|---|---|---|---|
| DE | 1 963 0469 | | 1/1998 |
| DE | 199 50 756 | | 8/2000 |
| DE | 101 03 000 | | 8/2002 |
| EP | 0 203 945 | B2 | 12/1986 |
| EP | 0 274 129 | B1 | 7/1988 |
| EP | 0 282 143 | | 9/1988 |
| EP | 0 364 787 | A1 | 4/1990 |
| EP | 0 505 686 | | 9/1992 |
| EP | 0 533 960 | | 3/1993 |
| EP | 0 596 145 | | 5/1994 |
| EP | 0 696 447 | A2 | 2/1996 |
| EP | 0 714 640 | | 6/1996 |
| EP | 0 797 963 | A2 | 1/1997 |
| EP | 0 947 180 | | 10/1999 |
| EP | 1 258 230 | | 11/2002 |
| EP | 1 266 638 | B1 | 12/2002 |
| EP | 1 277 449 | | 1/2003 |
| EP | 1 290 987 | A2 | 3/2003 |
| EP | 1 318 765 | | 6/2003 |
| EP | 1 470 834 | | 10/2004 |
| EP | 1 523 959 | A2 | 4/2005 |
| EP | 1 523 960 | A2 | 4/2005 |
| GB | 2277875 | A | 11/1994 |
| JP | 03-133446 | | 6/1991 |
| JP | 10-503663 | | 4/1998 |
| JP | 10-295823 | | 11/1998 |
| JP | 2001-190687 | | 7/2001 |
| JP | 2002-538932 | T | 11/2002 |
| JP | 2004-121343 | A | 4/2004 |
| WO | WO 94/27667 | A1 | 12/1994 |
| WO | WO 95/26695 | A2 | 10/1995 |
| WO | WO 95/29647 | A2 | 11/1995 |
| WO | WO 96/26689 | | 9/1996 |
| WO | WO 96/33677 | | 10/1996 |
| WO | WO 96/37167 | A1 | 11/1996 |
| WO | WO 96/39077 | | 12/1996 |
| WO | WO 97/10778 | | 3/1997 |
| WO | WO 97/46174 | | 12/1997 |
| WO | WO 97/48351 | | 12/1997 |
| WO | WO 98/20810 | | 5/1998 |
| WO | WO 98/37833 | | 9/1998 |
| WO | WO 98/58600 | | 12/1998 |
| WO | WO 99/01087 | | 1/1999 |
| WO | WO 99/65421 | | 12/1999 |
| WO | WO 00/12832 | A3 | 3/2000 |
| WO | WO 00/15151 | | 3/2000 |
| WO | WO 00/25841 | | 5/2000 |
| WO | WO 00/32136 | | 6/2000 |
| WO | WO 00/41649 | | 7/2000 |
| WO | WO 00/50116 | | 8/2000 |
| WO | WO 00/51525 | A1 | 9/2000 |
| WO | WO 00/56237 | | 9/2000 |
| WO | WO 00/62708 | | 10/2000 |
| WO | WO 00/72780 | | 12/2000 |
| WO | WO 01/26707 | | 4/2001 |
| WO | WO 01/34063 | | 5/2001 |
| WO | WO 01/70297 | | 9/2001 |
| WO | WO 01/91918 | | 12/2001 |
| WO | WO 02/085253 | | 10/2002 |
| WO | WO 02/098326 | | 12/2002 |
| WO | WO 03/022178 | | 3/2003 |
| WO | WO 03/047651 | | 6/2003 |
| WO | WO 03/051425 | | 6/2003 |
| WO | WO 03/075797 | | 9/2003 |
| WO | WO 004/017865 | | 3/2004 |
| WO | WO 2004/043299 | | 5/2004 |
| WO | WO 2004/043301 | | 5/2004 |
| WO | WO 2004/043510 | | 5/2004 |
| WO | WO 2004/052237 | A2 | 6/2004 |
| WO | WO 2004/087006 | | 10/2004 |
| WO | WO 2004/091441 | | 10/2004 |
| WO | WO 2005/009295 | | 2/2005 |
| WO | WO 2005/013853 | | 2/2005 |
| WO | WO 2005/023153 | | 3/2005 |
| WO | WO 2006/036939 | | 4/2006 |
| WO | WO 2006/047520 | | 5/2006 |
| WO | WO 2007/035805 | | 3/2007 |
| WO | WO 2007/053187 | | 5/2007 |
| WO | WO 2007/146411 | | 12/2007 |
| WO | WO 2008/005111 | | 1/2008 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

"Drug Delivery Stent With Holes Located on Neutral Axis" Research Disclosure, Kenneth Mason Publications, Hampshire, CB, No. 429, Jan. 2000, p. 13, XP00976354.

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

Chu et al., "Preparation of Thermo-Responsive Core-Shell Microcapsules with a Porous Membrane and Poly(N-isopropylacrylamide) Gates," J Membrane Sci, Oct 15, 2001; 192(1-2):27-39.

Tilley, "Biolimus A9-Eluting Stent Shows Promise," Medscape Medical News, Oct 5, 2004; retrieved from the internet: <http://www.medscape.com/viewarticle/490621>, 2 pages total.

Weir et al., "Degradation of poly-L-lactide. Part 2: increased temperature accelerated degradation," Proc Inst Mech Eng H. 2004;218(5):321-30.

\* cited by examiner

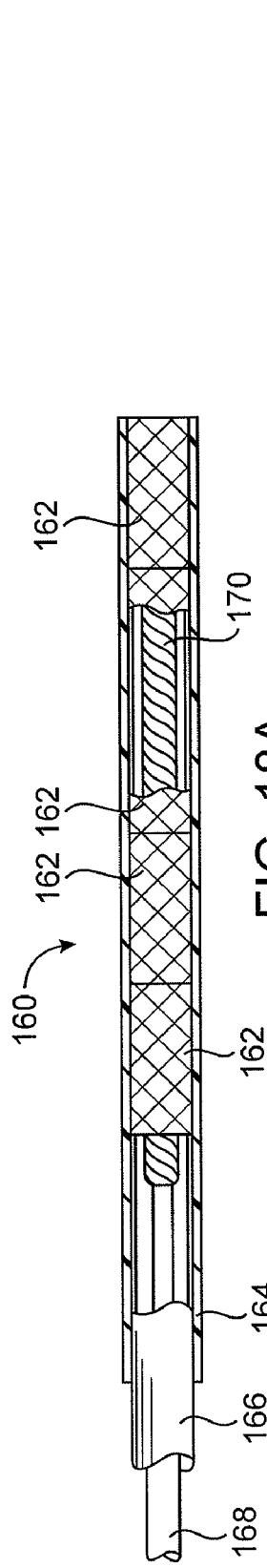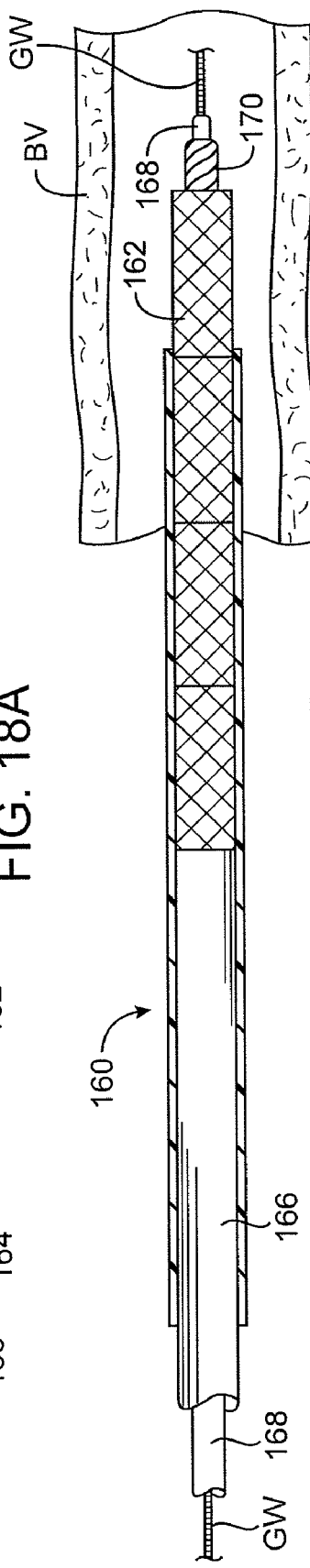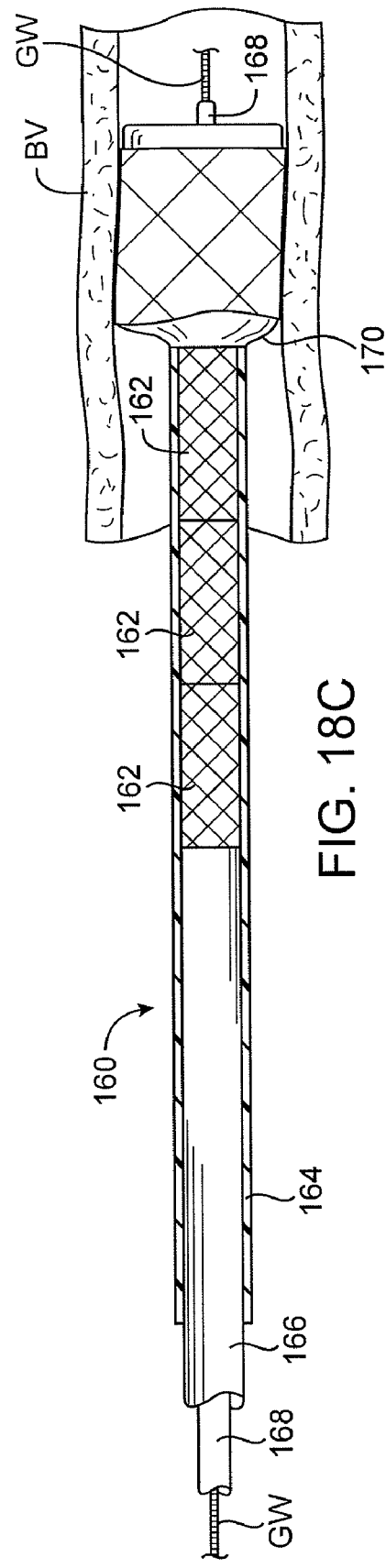
FIG. 18A
FIG. 18B
FIG. 18C

MULTIPLE INDEPENDENT NESTED STENT STRUCTURES AND METHODS FOR THEIR PREPARATION AND DEPLOYMENT

CROSS-REFERENCES TO RELATED APPLICATIONS

This application is a continuation of U.S. patent application Ser. No. 10/738,666 filed Dec. 16, 2003 which claims the priority benefit of U.S. Provisional Patent Application No. 60/440,839, filed Jan. 17, 2003, each of which the entire contents are incorporated herein by reference.

BACKGROUND OF THE INVENTION

1. Field of the Invention

The present invention relates generally to medical devices and methods. More particularly, the present invention relates to apparatus and methods for delivering a plurality of separate luminal prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or, even if survived, can cause damage to the heart which can incapacitate the patient.

While coronary artery bypass surgery can be an effective treatment for stenosed arteries resulting from atherosclerosis or other causes, it is a highly invasive procedure which is also expensive and which requires substantial hospital and recovery time. Percutaneous transluminal angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting, which involves the placement of a scaffold structure within an artery that has been treated by balloon angioplasty. The stent inhibits abrupt reclosure of the artery and has some benefit in inhibiting subsequent restenosis resulting from hyperplasia.

Presently available stents may be generally categorized as either "closed cell configurations" or "open cell configurations." Closed cell configurations are characterized by ellipses, ovals, and polygonal structures, such as closed boxes, rhomboids, diamonds, and the like, which open in the circumferential direction and shorten in the axial direction as the stent is expanded. Open cell configurations include zigzag and serpentine structures which may be formed as a plurality of discreet rings or may be formed from a single continuous wire or other element. Closed cell stents are advantageous in that they provide better coverage of the blood vessel wall when the stent is deployed. This is particularly advantageous in tightly curved segments of the vasculature where even stent coverage in both the axial and circumferential directions on the outer wall of the vessel has been shown to reduce restenosis. Such even coverage is also an advantage in achieving uniform delivery from drug eluting stents. In contrast, open cell stent configurations are generally more flexible than the closed cell configurations. Such flexibility is advantageous in the tortuous regions of the vasculature where enhanced flexibility can provide better conformance to the vessel being treated. Better conformance can reduce the stress on the vessel wall, particularly at the stent ends, and lead to reduced restenosis.

For these reasons, it would be desirable to provide improved stents and stent structures. In particular, it would be desirable to provide stents and stent structures which combine the improved wall coverage of closed cell stent structures with the increased flexibility of open cell stent structures. It would be still further desirable if such improved stent structures allowed a physician to optimize the length of vessel being treated in accordance with the nature of the disease, allowed for the delivery of both very short and very long stent structures, and optionally permitted delivery of stent structures at multiple contiguous and/or non-contiguous locations within a body lumen. At least some of these objectives will be met by the inventions described hereinafter.

2. Description of the Background Art

U.S. Pat. Nos. 6,200,337 and 5,870,381 describe stents having closed cell rings with overlapping portions connected by axial connecting members. U.S. Pat. No. 6,375,676 describes a stent having open cell rings with overlapping portions connected by axial connecting members. U.S. Patent Application Publication Nos. 2002/0188343 and 2002/0188347 describe expandable stents having interconnecting elements which interlock circumferentially adjacent bridges between axially adjacent stent segments. U.S. Pat. No. 4,580,568 describes the sequential placement of a plurality of zig-zag ring stents where the stents may optionally be overlapped (FIGS. 7 and 8). U.S. Pat. No. 6,319,277 describes a stent formed from a single element into a plurality of nested "waves." U.S. Pat. No. 5,554,181 describes a stent formed from a single element into partially overlapping windings. Other patents of interest include U.S. Pat. Nos. 6,312,458; 5,879,370; 5,755,776; 5,507,771; and 5,104,404. U.S. Pat. No. 6,258,117 B1 describes a stent having multiple sections connected by separable or frangible connecting regions. Optionally, the connecting regions are severed after the stent structure has been implanted in the blood vessel. U.S. Pat. Nos. 5,571,086; 5,776,141; and 6,143,016 describe an expandable sleeve for placement over a balloon catheter for the delivery of one or two stent structures to the vasculature. U.S. Pat. No. 5,697,948, describes a catheter for delivering stents covered by a sheath.

BRIEF SUMMARY OF THE INVENTION

The present invention provides methods and apparatus for prosthesis placement, such as stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable prostheses and scaffolds which are designed to be intraluminally introduced to a treatment site and expanded in situ to apply a radially outward force against the inner wall of the body lumen at that site. The stents and prostheses of the present invention commonly comprise a closed or, less preferably, an open lattice structure, and are typically formed from a malleable or elastic metal. When formed from a malleable metal, such as stainless steel, gold, platinum, titanium, and super alloys, the stents will typically be expanded by a balloon which causes plastic deformation of the lattice so that it remains opened after deployment. When formed from an elastic metal, including super elastic metals such as nickel-titanium alloys, the lattice structures will usually be radially constrained when delivered and deployed by releasing the structures from such radial constraint so that they "self-expand" at the target site. When the stent or lattice structures are covered with a fabric or polymeric membrane covering, they are commonly referred to as grafts. Grafts may be used for the treatment of aneurysms or other conditions which require placement of a non-permeable or semi-permeable barrier at the treatment site. The terms "stent" and "stent structures" refer broadly to all radially expansible stents, grafts, and other scaffold-like structures which are intended for deployment within body lumens.

The stents and stent structures of the present invention may have any of a variety of common constructions, including closed cell constructions such as expansible ovals, ellipses, box structures, expandable diamond structures, expandable rhomboid structures, as well as other regular and irregular polygonal structures, etc. In addition, the closed cells may have complex slotted geometries, such as H-shaped slots, I-shaped slots, J-shaped slots, etc. Suitable open cell structures include zigzag structures, serpentine structures, and the like. Such conventional stent structures are well described in the patent and medical literature. Specific examples of suitable stent structures are described in the following U.S. Patents, the full disclosures of which are incorporated herein by reference: U.S. Pat. Nos. 6,315,794; 5,980,552; 5,836,964; 5,527,354; 5,421,955; 4,886,062; and 4,776,337. Preferred structures are described herein with reference to FIGS. 4 and 5.

According to one aspect of the present invention, stents will comprise a plurality of independent expansible rings each having a length of 1 mm or greater, usually 2 mm or greater, and sometimes of 3 mm or greater, usually being in the range from 1 mm to 10 mm, typically from 2 mm to 7 mm, more typically from 2 mm to 5 mm. The use of such short ring lengths is advantageous since the overall stent length will be a multiple of the ring length.

The methods and apparatus of the present invention will provide for the deployment of a plurality of stents or other prostheses from a common stent delivery catheter. Usually, the number of delivered stents will be in the range from 2 to 50, typically from 3 to 30, and most typically from 3 to 25. As more stents are placed on the delivery catheter, the individual stent length will often be somewhat less, although this is not necessarily the case in all instances. The multiple prostheses may be deployed individually or in groups of two or more at a single location or at multiple spaced-apart locations in the body lumen or lumens.

In another aspect of the present invention, stent structures will comprise a plurality of radially expansible rings, as generally described above, arranged along an axial line. Expansible rings are arranged adjacent to each other and will include axially extending elements which interleave or nest with similarly axially extending elements on adjacent rings. By "interleaved" it is meant that the axially extending elements on adjacent rings will interpenetrate with each other in an axial direction, at least prior to stent expansion and preferably even after stent expansion. Usually, the interpenetrating elements will not overlap, i.e., be positioned one over another in the radial direction, but it is possible that in some implementations there may be some overlapping prior to or even after expansion. The axial interpenetration will be at least 0.1 mm, usually being at least 1 mm, and often being in the range from 1 mm to 5 mm, and will of course depend on the axial length(s) of the adjacent ring(s). Expressed as a percentage, the axial length of the axially extending elements will usually be at least 5% of the axial length of the ring, usually being from 5% to 50%, and preferably being from 20% to 30%.

Preferably, the axially extending elements on adjacent rings will interleave without interlocking so as to permit axial separation between the adjacent rings prior to expansion of the rings. However, axially extending elements may, in some instances, also interpenetrate in a peripheral direction prior to expansion. Such peripheral interpenetration can provide axial interlocking of the axially adjacent expansible rings prior to expansion. It will usually be desirable or even necessary that the peripheral interpenetration be relieved during radial expansion of the stent structures so that the independent rings be released from each other when deployed. In other instances, however, a tether or other types of links may be provided to interconnect or otherwise restrain the rings even after expansion and deployment.

It is not necessary that all adjacent rings be unconnected, although at least two, and preferably three, four, five, eight, ten, or more adjacent rings will be unconnected. Thus, some (but fewer than all) of the adjacent rings of the stent structures may have ties or links therebetween, including flexible or non-flexible (deflectable) ties or links. The axially adjacent rings, however, will usually not be connected, although in some cases they may have easily separable or non-permanent connections as described in more detail below. Each expansible ring will preferably comprise expansible closed cell structures, as set forth above. Less preferably, the expansible rings may comprise expansible open cell structures, as set forth above. The lengths and diameters of the individual rings have been set forth generally above. The stent structure will typically comprise from 2 to 50 individual rings, usually from 3 to 30 individual rings, and often from 3 to 25 individual rings.

The spacing between adjacent rings may be uniform or non-uniform, preferably being uniform. In some cases, it is desirable that the edges of the adjacent rings be spaced-apart by a uniform distance in the axial direction, typically at least 0.1 mm, usually being from 0.1 mm to 0.5 mm, prior to stent expansion. In other situations, it will be preferred that the adjacent rings be in contact with each other at discreet points or along continuous sections of the edges. In some cases, the stent structures will be configured to shorten upon expansion to increase the spacing between rings. It is usually preferable that the edges of the adjacent rings not overlap, at least prior to deployment. Deployment of the stents, particularly in curved and tortuous luminal regions, may sometimes result in touching and overlapping of the stent rings.

The stent structures may be modified in a variety of ways which are used with other conventional stents. For example, some or all of the radially expansible rings may releasably carry a biologically active agent, such as an agent which inhibits hyperplasia. Exemplary anti-hyperplasia agents include anti-neoplastic drugs, such as paclitaxel, methotrexate, and batimastal; antibiotics such as doxycycline, tetracycline, rapamycin, everolimus and other analogs and derivatives of rapamycin, and actinomycin; amino suppressants such as dexamethasone and methyl prednisolone; nitric oxide sources such as nitroprussides; estrogen; estradiols; and the like.

In another aspect of the present invention, a stent deployment system comprises an elongate carrier having a central axis and including a plurality of radially expansible rings arranged over a surface thereof. At least some of the radially expansible rings will have the features and characteristics just described with respect to the present invention. The elongate carriers of the stent deployment systems will typically comprise a radially expansible balloon having an outer surface where the radially expansible rings are disposed over the outer surface of the balloon. In such cases, the balloon may comprise a single inflation chamber in which case all of the rings will be expanded simultaneously. Alternatively, the balloon may comprise a plurality of independently inflatable chambers so that individual expansible rings may be deployed separately from the other rings.

The elongated carrier of the stent deployment system may alternatively comprise a carrier tube having an inner surface which carries and constrains the radially expansible rings. In such cases, the expansible rings will usually be self-expanding, i.e., held in a radially constrained configuration by the carrier tube prior to release and expansion at a luminal target site. Usually, the carrier tube structures will further comprise a pusher tube arranged to axially advance the radially expansible rings from the carrier tube. The elongated carrier may still further comprise a balloon arranged to receive and expand individual rings as they advance from the carrier tube, in which case the carrier may be used for delivering the formable (balloon-expansible) stent structures. However, such a balloon may also be used with self-expanding stent structures to control or enhance expansion, to perform predilatation of a lesion prior to stent deployment, or to further expand the stent structures and dilate the vessel lumen after the structures have self-expanded.

In a further aspect of the present invention, multiple independent stent rings are arranged on a carrier by the following methods. An elongated carrier structure is provided and a plurality of radially expansible rings comprising axially extending elements are mounted on the carrier structure such that the axially extending elements on adjacent rings interleave or nest after they are mounted. The number of rings mounted on the carrier is selected to provide a desired overall stent length, and the number of rings is typically in the ranges set forth above, providing overall stent lengths in the range from 6 mm to 120 mm, usually from 9 mm to 100 mm, and typically from 12 mm to 50 mm. Other aspects of the individual radially expansible rings have been described above.

In yet another aspect of the present invention, methods for stenting a body lumen comprise delivering to the body lumen a stent structure having a plurality of radially expansible rings. The rings are as described above with respect to other aspects of the present invention, and at least some of the rings are expanded within the body lumen so that the axially extending elements open and axially move apart from each other as they radially expand. Preferably, the length of the axially extending elements and degree of radial expansion will be selected so that the elements remain interleaved even after being fully expanded within the body lumen. Such an interleaving structure enhances the continuity of lumenal wall coverage provided by the deployed stent structure. Target body lumens are typically blood vessels, more typically arteries, such as coronary arteries. The rings may be delivered simultaneously, typically using a single inflatable balloon, or sequentially, typically using a carrier tube, pusher tube and optionally deployment balloon. Methods may be used for delivering from 3 to 50 rings, usually from 3 to 30 rings, and typically from 3 to 25 rings, to cover a luminal length in the range from 6 mm to 120 mm, usually from 9 mm to 100 mm, and typically from 12 mm to 50 mm.

BRIEF DESCRIPTION OF THE DRAWINGS

FIGS. 18A-18D illustrate deployment of a plurality of a expansible rings which form a stent structure according to the present invention using a delivery tube and pusher tube in combination with an expansion balloon.

DETAILED DESCRIPTION OF THE INVENTION

The present invention provides apparatus, systems, and methods for preparing and delivering stent structures comprising a plurality of "separate" or "discreet" radially expansible ring segments. By "separate" or "discreet," it is meant that the ring segments are unconnected (or easily disconnected) at the time they are delivered to a target body lumen. Usually, the ring segments will be closely packed to provide a relatively high degree of vessel wall coverage after they are expanded. By disconnecting the adjacent segments, however, such a tightly packed structured can retain a very high degree of flexibility permitting delivery and conformance in even highly torturous regions of the vasculature and other body lumens.

The ability to closely pack the expansible ring segments and achieve a high degree of vessel wall coverage is achieved at least partly because at least some of the axially adjacent rings comprise axially extending elements which interleave or nest with axially extending elements on an adjacent connected ring. Usually, the axially extending elements will be formed from a radially expansible portion of the ring, e.g., the element will be part of the closed cell structure or open cell structure as described in more detail hereinbelow. As these expansible sections will typically foreshorten as they are radially expanded, interleaving and nesting the segments on adjacent rings prior to expansion minimizes or preferably eliminates any gaps in coverage after the stent is expanded, as described in more detail below.

The stent structures of the present invention may be fabricated as either balloon-expansible or self-expanding stents according to methods well known in the art. Typical deformable materials suitable for fabricating balloon-expansible stent structures include 316L stainless steel, gold, platinum, cobalt chrome, platinum, and the like. Suitable resilient materials for self-expanding stents include nickel titanium alloys, various spring stainless steel alloys, Eligloy® alloy, and the like. It will also be possible to form the stent structures of the present invention from both natural and synthetic polymers. Natural polymers include collagen, gelatin, chitin, cellulose, and the like. Suitable synthetic polymers include polyglycolic acids (PGA), polylactic acids (PLA), poly ethylene glycols (PEG), polyamides, polyimides, polyesters, and the like. In some instances, it would be possible to form different radially expansible segments from different materials in order to achieve different properties.

Figure 2:
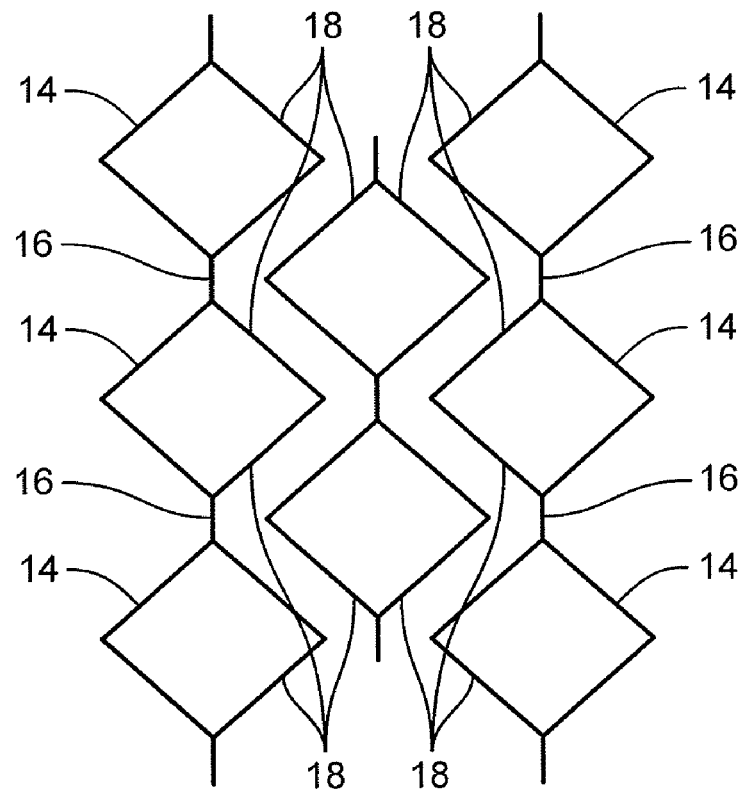
FIG. 2 illustrates the stent structure of FIG. 1 shown in its radially expanded configuration.
Figure 3:
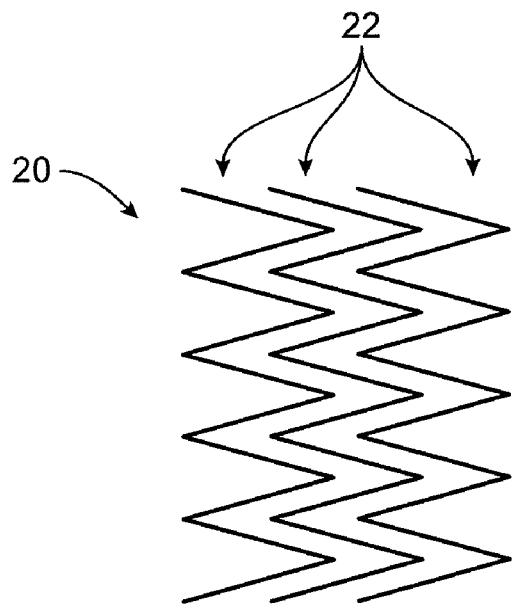
FIG. 3 illustrates a stent structure constructed in accordance with the principles of the present invention comprising a plurality of open cell expansible rings.
Figure 4:
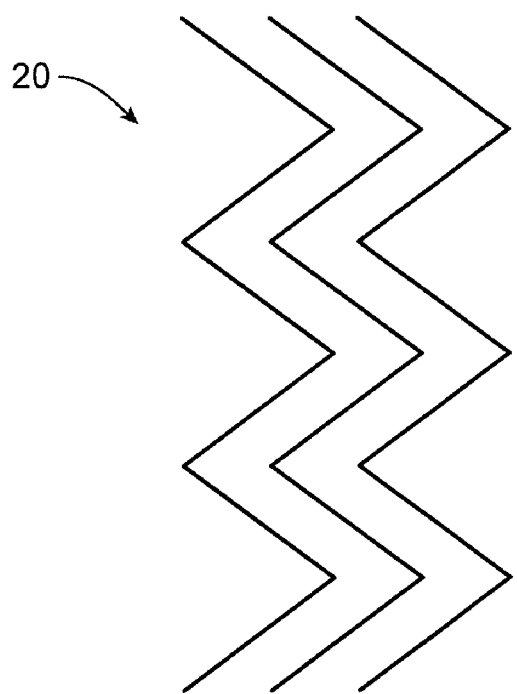
FIG. 4 illustrates the stent structure of FIG. 3 shown in its radially expanded configuration.

The stent structures will comprise a plurality of the individual radially expansible ring segments with typical dimensions, numbers, and the like, described above in the summary. The plurality of ring segments will be arranged prior to delivery, in a manner suitable for delivery to and deployment within a target blood vessel or other body lumen. Usually, the plurality of radially expansible rings will be arranged along an axial line, typically defined by a deployment balloon, a delivery tube, or some combination thereof. The expansible ring segments will be arranged so that the axially extending elements on each of the segments is interleaved with corresponding axial extending elements on adjacent but unconnected ring segments. Referring now to FIGS. 1-4, such arrangements will be generally described for both closed cell ring structures (FIGS. 1 and 2) and open cell ring structures (FIGS. 3 and 4).

Figure 1:
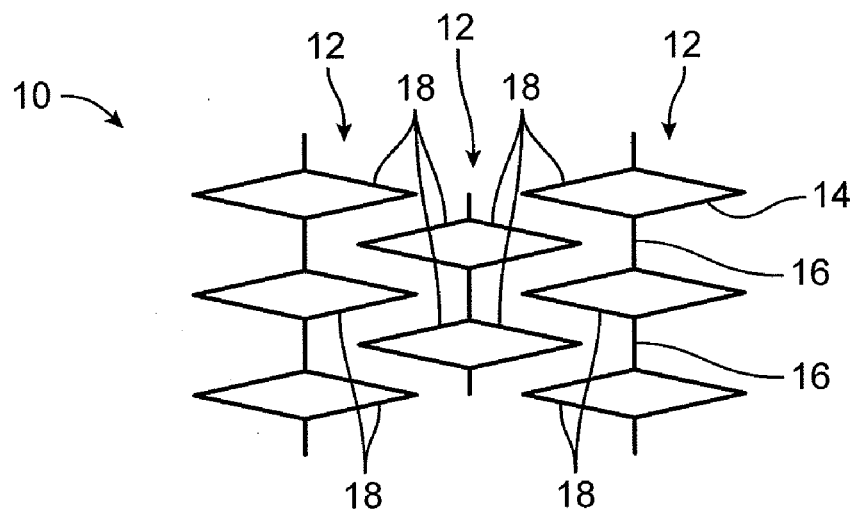
FIG. 1 is a schematic illustration of a stent structure according to the present invention comprising a plurality of closed cell ring structures.

In FIG. 1, a portion of a stent structure 10 comprising a plurality of radially expansible rings 12 is illustrated. Each radially expansible ring 12 includes a plurality of closed rhomboid or diamond structures 14 circumferentially joined by connectors 16. It will appreciated that the stent structure 10 is shown in a "rolled-out" configuration, and that only a portion of the structure is depicted for simplicity. Usually, the stent structure would contain a greater number of expansible rings 12, and each ring would include a larger number of rhomboid cells.

Of particular importance to the present invention, FIG. 1 illustrates that each rhomboid cell 14 includes an axially extending element 18 which interleaves with a similar element on an adjacent ring structure. This interleaved structure permits a very close packing of the rings without the need to physically attach the rings. Moreover, when the stent structure is radially expanded, as shown in FIG. 2, the axially extending elements 18 will usually continue to axially interleave which increases the coverage of the body lumen wall being treated.

Figure 2A:
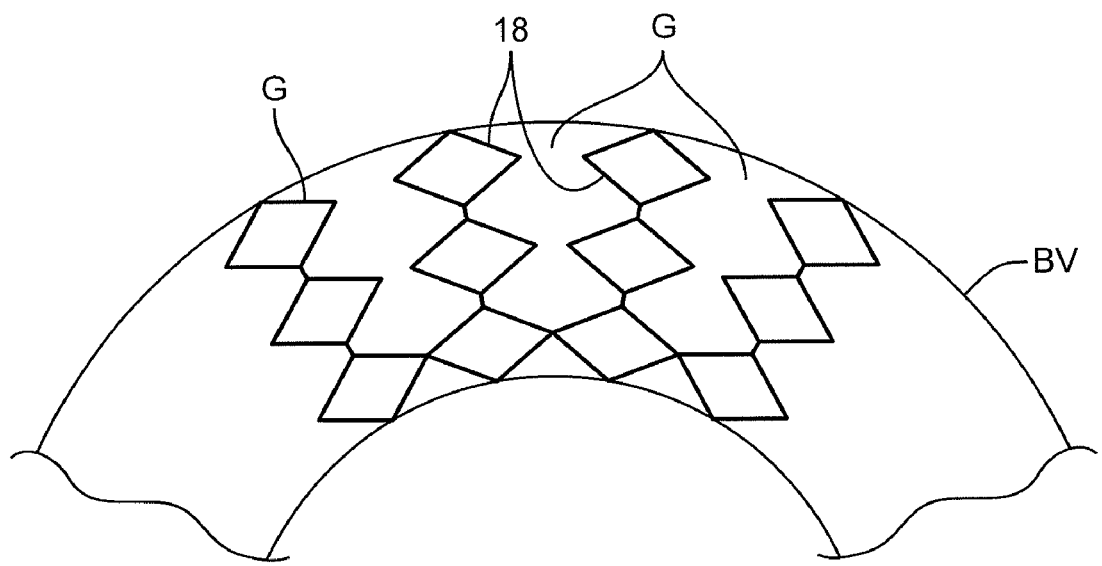
FIGS. 2A and 2B illustrate the difference in deployed configuration of non-nested and nested stent structures, respectively.
Figure 2B:
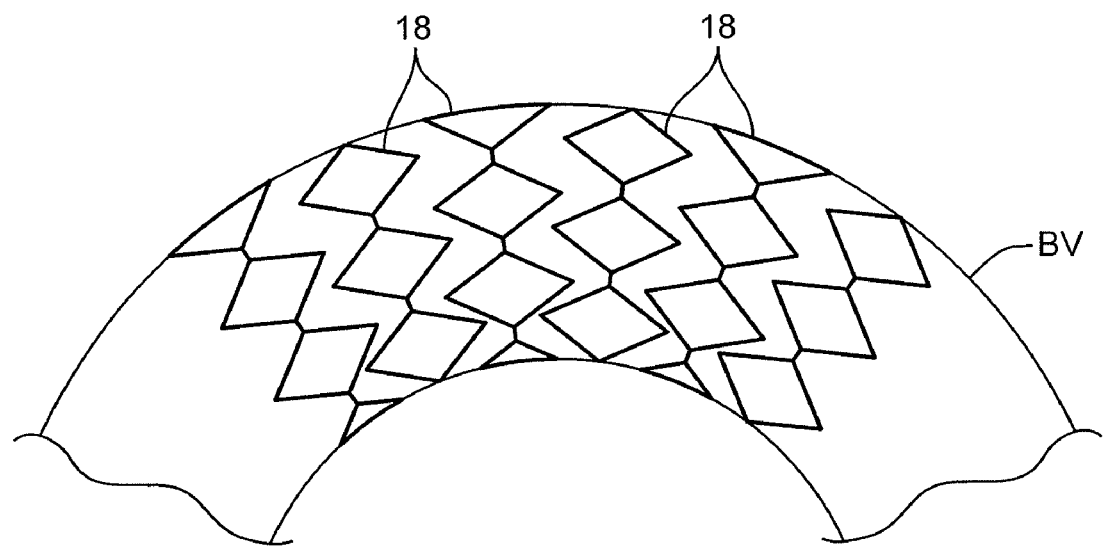

The advantages of the present invention are particularly apparent in curved blood vessels BV, as illustrated in FIGS. 2A and 2B. An expanded, non-interleaved multiple ring stent is shown in FIG. 2A. Substantial gaps G appear between the axially extending elements 18 on the large diameter side of the curved vessel segment. In contrast, the nested stent configurations of the present invention are able to maintain interleaving of the axially extending elements 18, even on the large diameter side of the curved vessel segment, as shown in FIG. 2B. While the present invention cannot assure that gaps will always be eliminated, the number and extent of the gaps will at least be reduced, thus improving wall coverage.

A similar result can be achieved with a stent structure 20 comprising a plurality of open cell zigzag ring structures 22, shown in FIGS. 3 and 4. Each zigzag ring includes axially extending elements which alternate directions, and the rings are arranged so that the elements are "nested" as shown in FIG. 3. After radially expansion of the stent structure 20, the nested axially extending elements of the rings 22 remain generally overlapping, as shown in FIG. 4, even when the stent has undergone significant radial expansion. While prior stent structures have utilized nested zigzag structures, they have generally either connected adjacent structures or utilized only a single filament for forming such structures. In neither case can the flexibility achieved by the present invention in combination with the ability to selectively deliver independent radially expansible segments be achieved.

Figure 5:
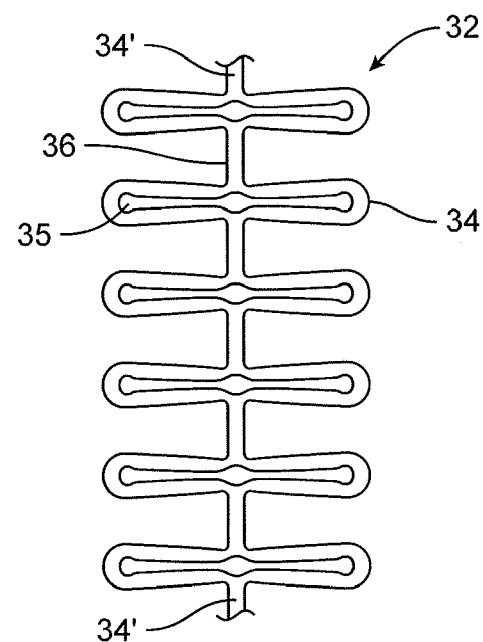
FIG. 5 illustrates a first exemplary expansible ring structure in accordance with the principles of the invention.
Figure 6:
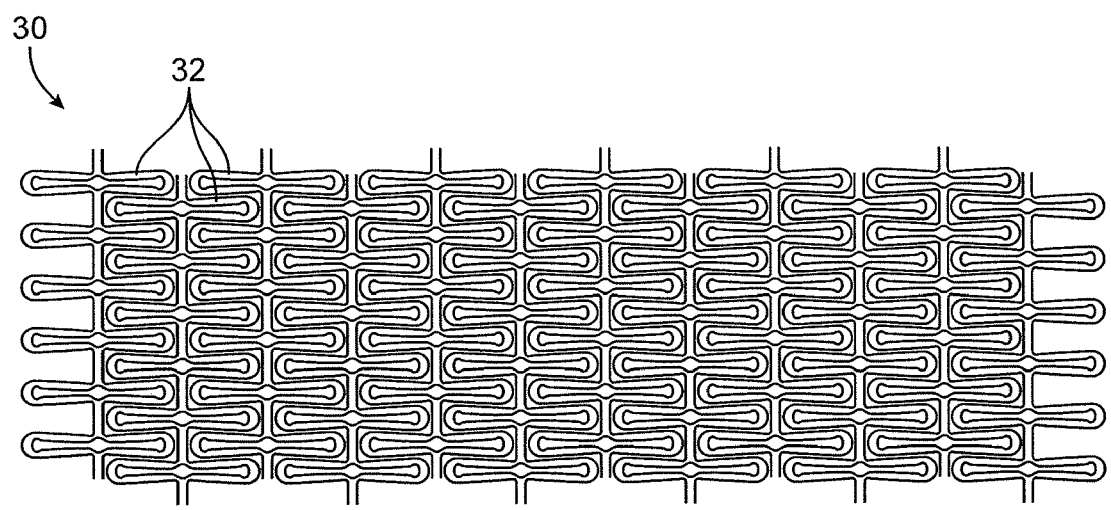
FIG. 6 illustrates a stent structure comprising a plurality of the ring structures of FIG. 5, shown in a rolled out radially collapsed configuration.
Figure 7:
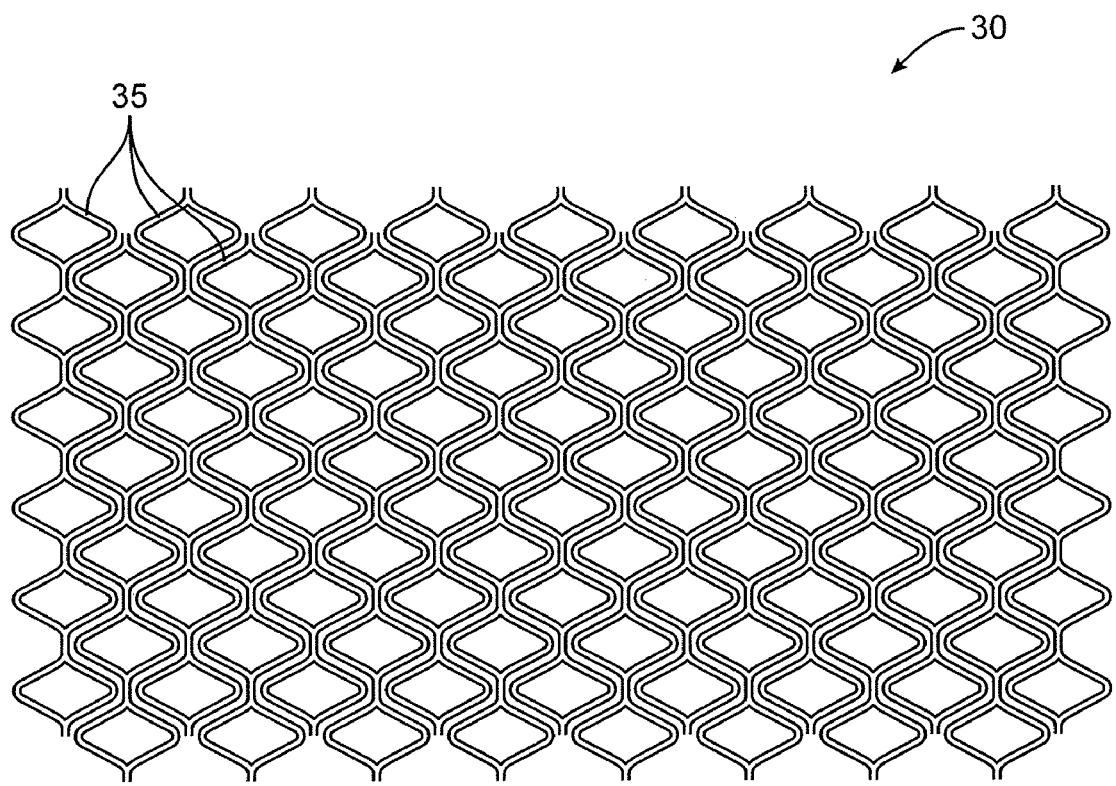
FIG. 7 illustrates the stent structure of FIG. 6 shown in its radially expanded configuration.

Referring now to FIGS. 5-7, a particular stent structure 30 comprising a plurality of radially expansible rings 32 is illustrated. Each ring 32, as shown in FIG. 5, comprises a plurality of closed cell boxes 34 joined at their midpoints by circumferentially directed connectors 36. Each box 34 includes a central opening 35 which is generally an axial cut enlarged at each end and in the middle. As with prior illustrations, the ring structure 32 is shown in its rolled-out or flattened configurations. In the actual stent structure, the ring would be rolled so that the "broken" connectors 34' are in fact connected to form a cylindrical shape. The "bow tie" shape of the central opening 35 is advantageous as it permits maximum radial compression of the stent while minimizing both the delivery profile and the stress relief of the stent during expansion in the body lumen.

FIG. 6 illustrates the very tight packing of the stent structure 30 that can be achieved. The stent structure 30 in FIG. 6 is in its pre-deployment configuration as it would be when placed over a balloon or within a delivery tube, as described in more detail hereinbelow. It can be seen that virtually all of the available area for carrying the stent is covered. Thus, when the stent is expanded as shown in FIG. 7, the area of the blood vessel or other luminal wall will be maximized. Moreover, this very close packing of the stent is achieved while concurrently providing a very high degree of flexibility while the stent is being delivered and conformability after the stent is deployed. Such flexibility results in large part from the fact that the adjacent rings are unconnected and free to move relative to each other as the stent is delivered and deployed. Coverage in curved vessels will be improved with the specific design of FIGS. 6 and 7 generally as shown in FIGS. 2A and 2B.

Figure 6A:
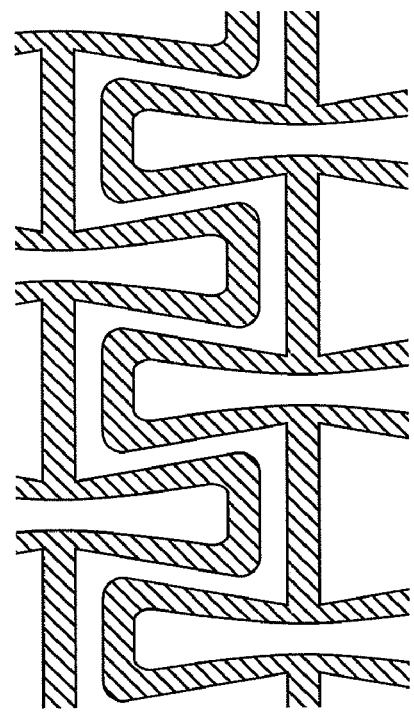
FIGS. 6A and 6B illustrate variations on the ring structure of FIG. 6, where the variations are chosen to inhibit axial separation of the ring structures prior to deployment.
Figure 6B:
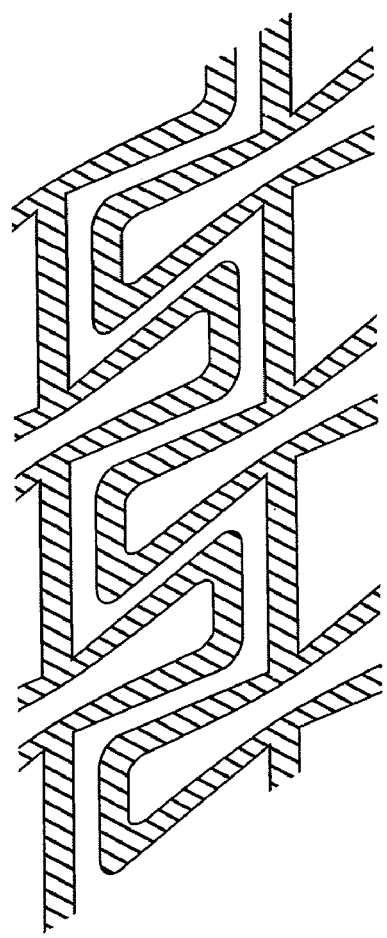

Axial separation of the rings 32 of stent structure 30 can be inhibited by modifying the ring geometries in a variety of ways, such as shown in FIGS. 6A and 6B. In FIG. 6A, the boxes 34a are fabricated (or deformed after fabrication) to collapse near the centers so that they form "bow tie" structures, with enlarged ends 34b interlocking. Alternatively, the boxes 34c can be inclined relative to the axial direction, as shown in FIG. 6B, to also provide interlocking of adjacent rings prior to deployment. Such inclination can be used with at least most of the embodiments of the present invention to improve axial retention. In addition, other patterns, such as chevrons, interleaved sigmoidal shapes, and the like could also be used to provide the desired interlocking prior to stent expansion.

Figure 8:
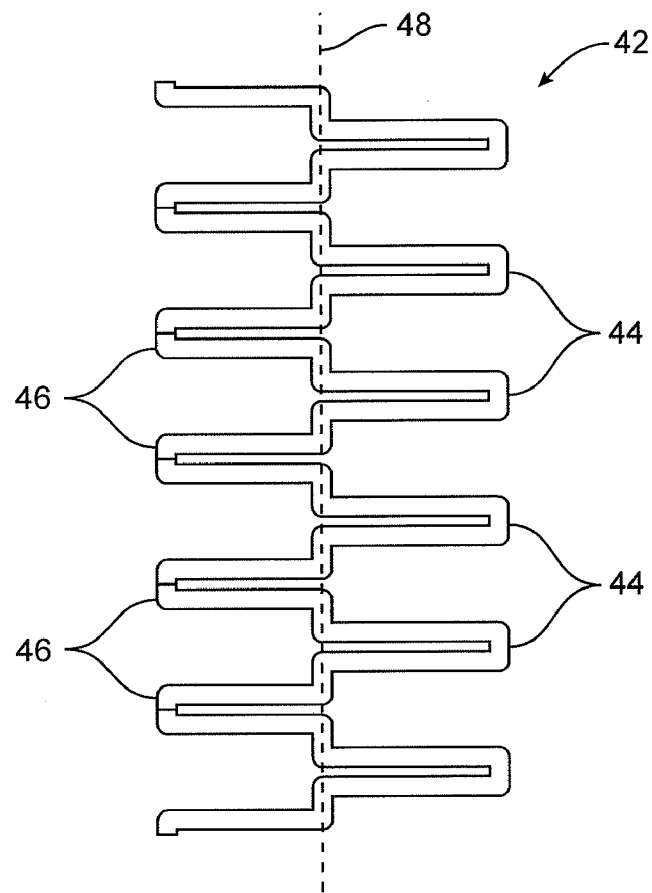
FIG. 8 illustrates a second exemplary expansible ring structure in accordance with the principles of the present invention.
Figure 9:
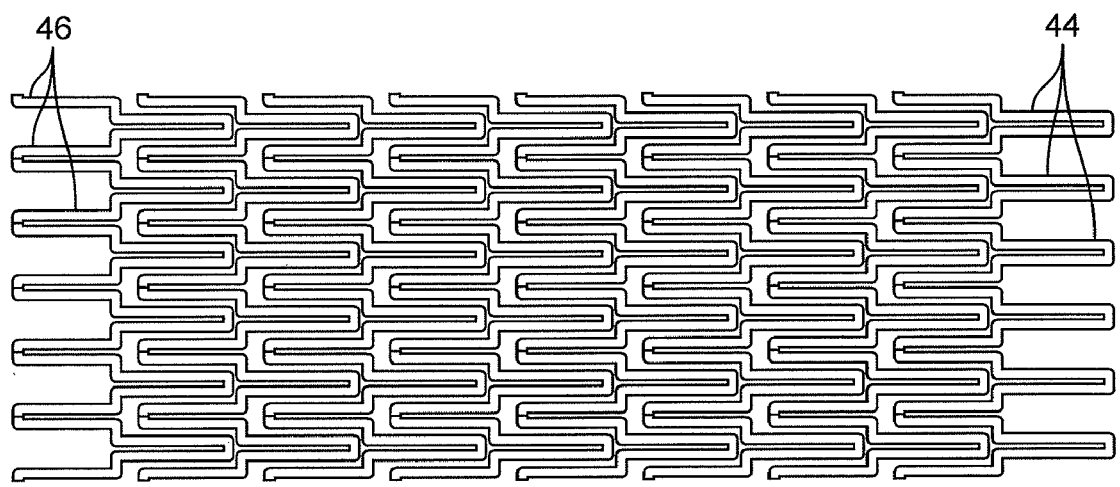
FIG. 9 illustrates a stent structure comprising a plurality of the rings of FIG. 8.
Figure 10:
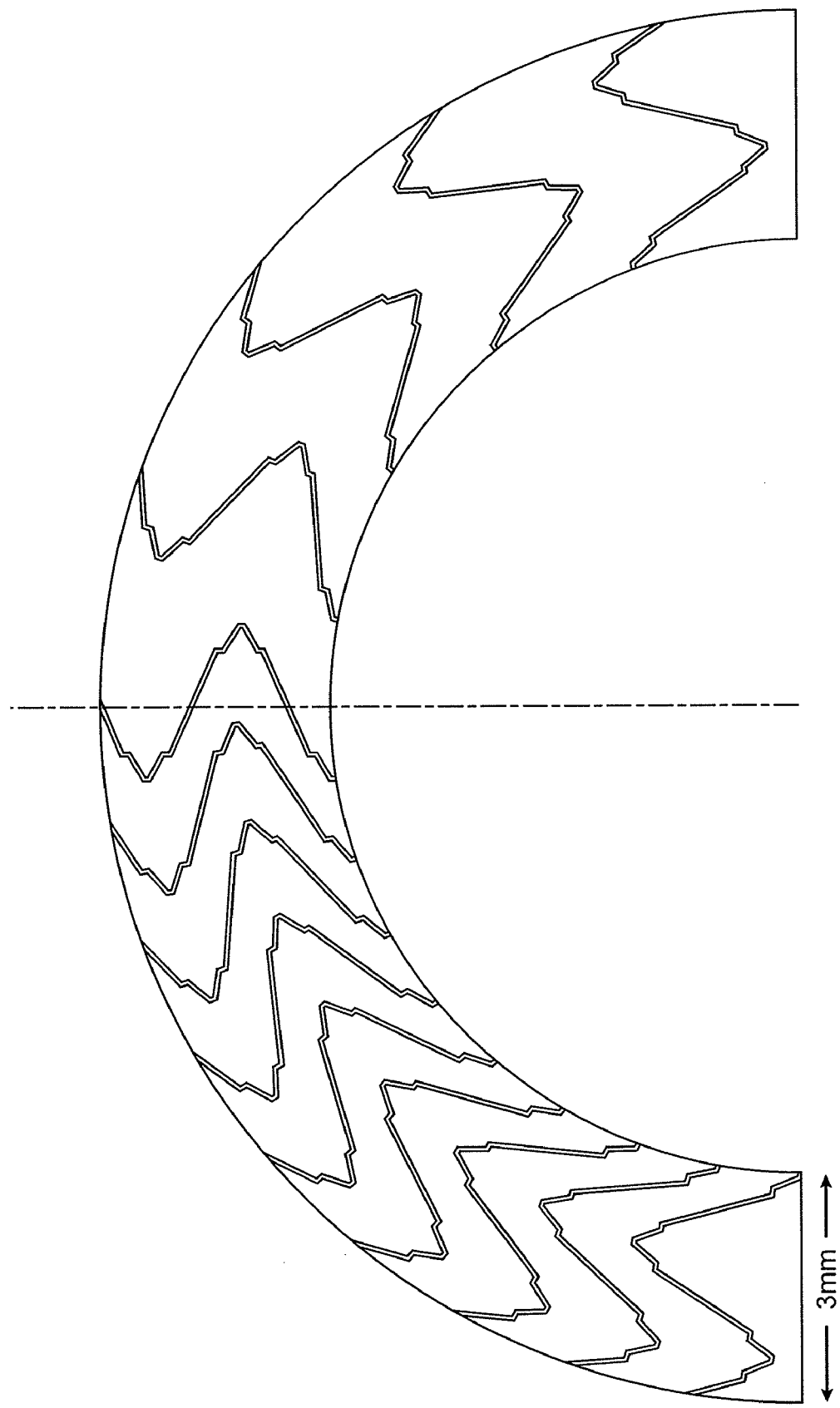
FIG. 10 illustrates the stent structure of FIG. 8 in its radially expanded configuration.
Figure 11:
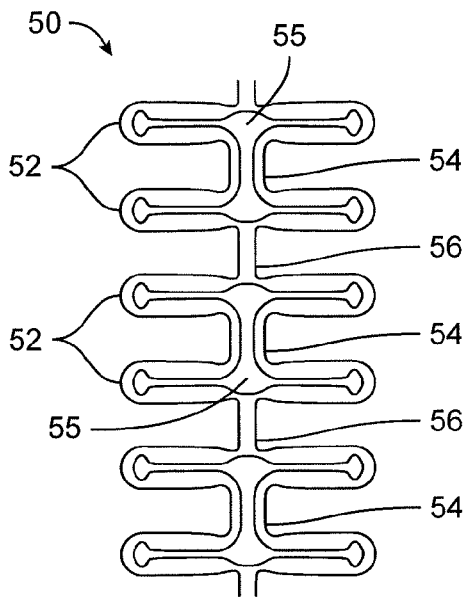
FIGS. 11-14 illustrate further exemplary expansible ring structures in accordance with the principles of the present invention.

Referring now to FIGS. 8-10, a similar degree of wall coverage and flexibility can be achieved with open cell stent structures. Stent structure 40 (FIG. 9) comprises a plurality of open cell expansible rings 42 formed in a "castellated" pattern, as shown in more detail in FIG. 8. The castellations comprise narrow U-shaped loops 44 and 46 which alternatively extend in a right hand direction (loop 44) and left hand direction (loop 46) relative to a circumferential center line 48. The rings 42 are arranged so that the loops 44 and 46 overlap, as shown in FIG. 9, to form a tightly packed configuration. When expanded, as shown in FIG. 9, the loops 44 and 46 continue to overlap to provide a very high degree of vessel wall coverage, as shown in FIG. 10. The open cell configuration of FIGS. 8-10 will also improve coverage in curved vessels, minimizing gaps as discussed previously. The length of the open cells will be in the range from 0.5 to 10 mm, usually from 2 to 5 mm.

Referring now to FIGS. 11-14, additional embodiments of the radially expansible ring segments are illustrated. As with prior illustrations, the ring segments are shown in their pre-deployed configuration in a rolled-out manner. Ring structure 50 of FIG. 11 comprises a plurality of closed cell box elements 52 joined by circumferential connectors 54 and 56. Ring 50 is similar to ring 32 of FIG. 5, except that the circumferential connectors 54 are split to form H-shaped slots 55 which span pairs of adjacent box structures 52 and the intermediate connectors 54 form a single, larger cell structures. Such larger openings are advantageous when stenting in blood vessels with side branches which must be kept open. In particular, the side branches may be accessed by opening the slots 55 with a balloon structure. In contrast, the cell pattern of stent 32 (FIG. 5) provides a greater coverage that may be of particular importance with drug eluting stents.

Figure 11A:
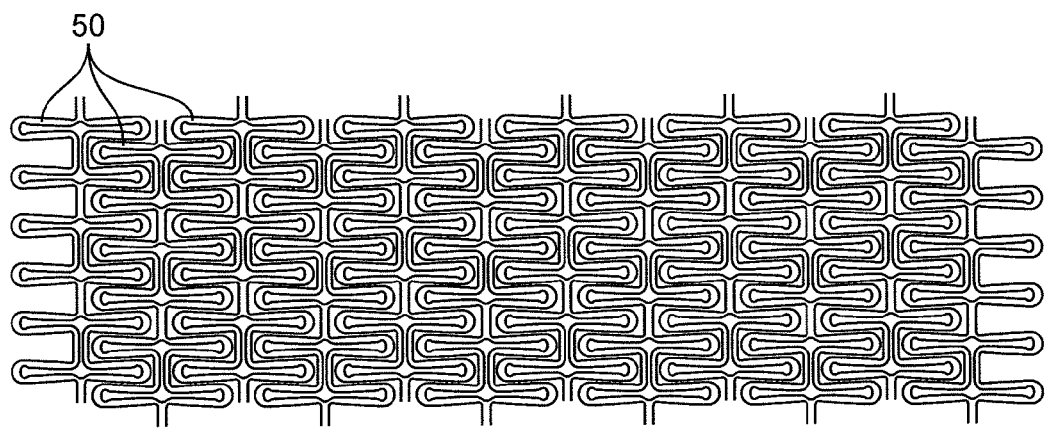
Figure 11B:
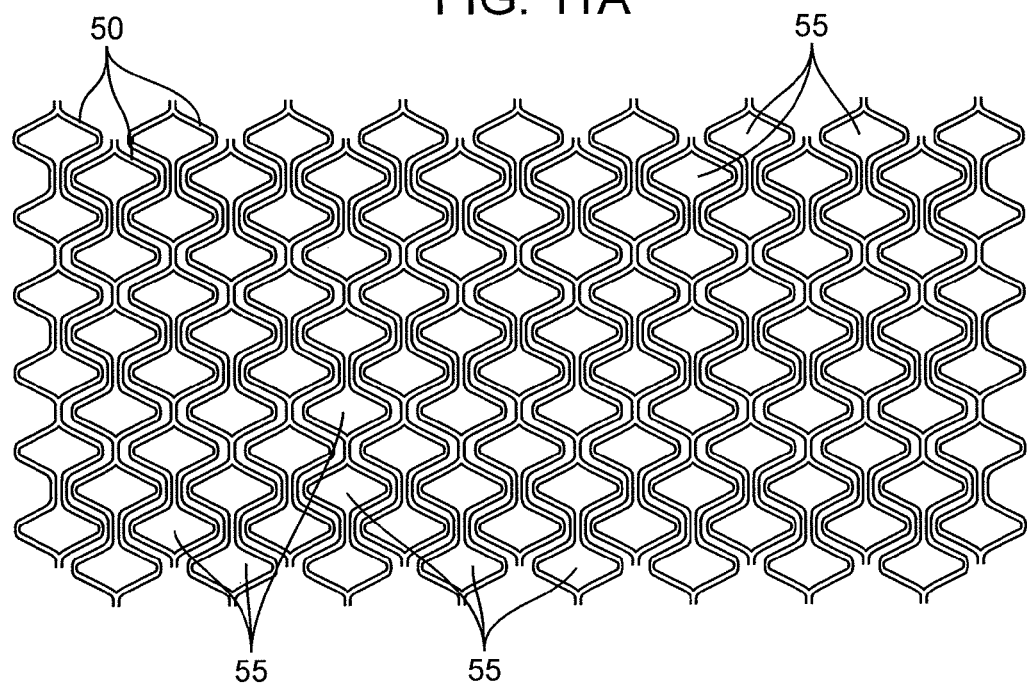
Figure 11C:
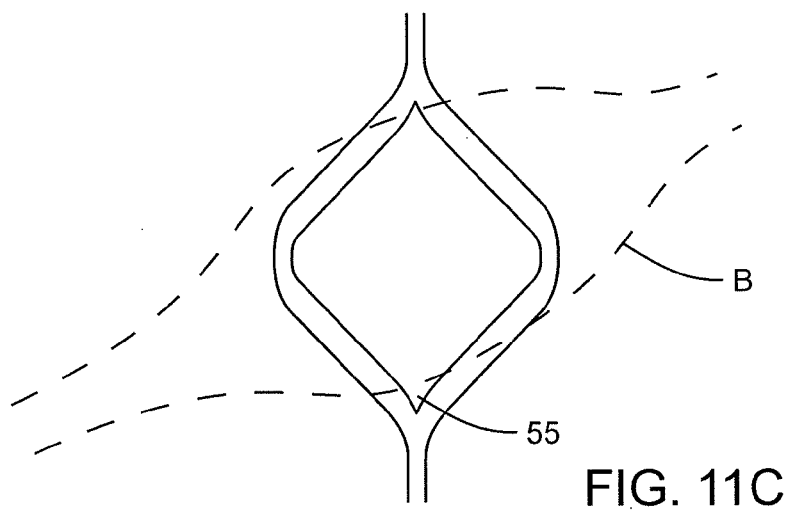

Stent structures comprising multiple rings 50 are shown in their unexpanded and expanded configuration in FIGS. 11A and 11B, respectively. Of particular note, the open slots 55 (FIG. 11B) provide for significant additional expansion (via balloon dilation or other subsequent intervention) in order to provide access to a side branch or for any other purpose. A further expanded slot 55 is shown in FIG. 11C, as expanded by balloon B.

Figure 12:
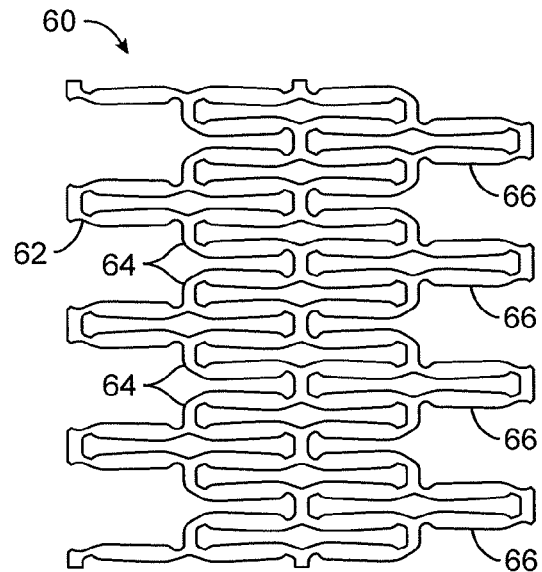

Ring structure 60 of FIG. 12 comprises a plurality of interconnected box structures 62, 64, and 66. Each of the box structures shares common axial struts or beams, but the axially offset nature of the three box structures permits radial expansion. Moreover, the box structures 62 and 66 provide the axially extending elements which may be interleaved in forming a stent structure from a plurality of the rings 60. Axially extending elements 62 and 66 interleave and mate so that interleaved extending elements of adjacent stents can be interference fit with each other to provide a friction fit which inhibits separation of the stents, or be kept out of contact to allow for separation. Furthermore, extending elements can deflect radially inward which will provide additional adherence to an expandable delivery balloon and increased stent retention.

Figure 13:
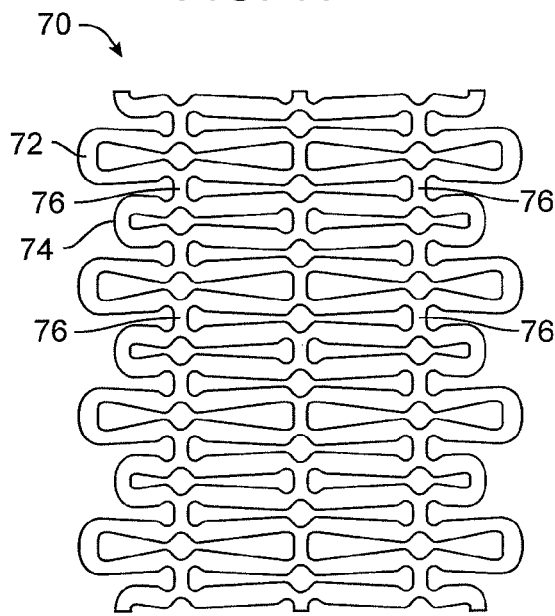

Ring structure 70 in FIG. 13 comprises paired, symmetric box structures 72 and 74 joined by short circumferential connectors 76. Each of the box structures 72 and 74 define a long and a short axially extending member which can be aligned with each other when forming a stent structure from a plurality of the rings 70. This particular structure will provide good adherence to an expandable delivery balloon during deployment and have many of the same advantages as the embodiment of FIG. 12.

Figure 14:
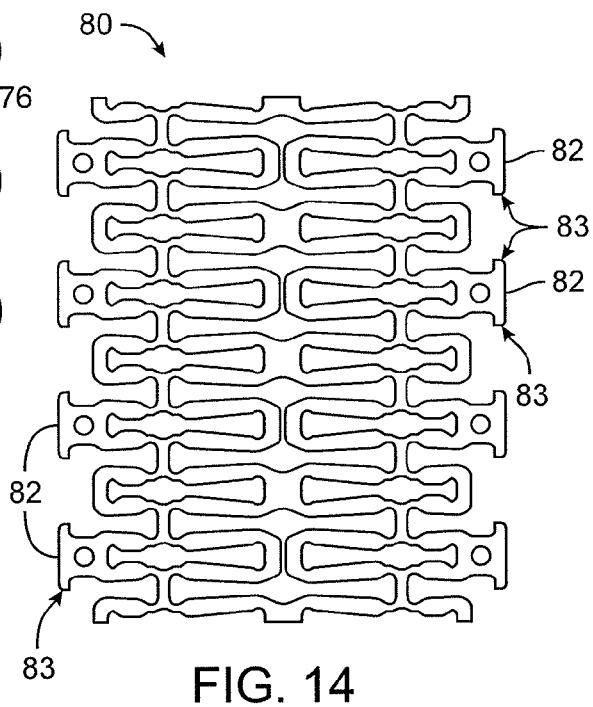

Ring structure 80 of FIG. 14 is similar to that of ring structure 70 of FIG. 13, except that the "longer" rings terminate in a retainer, such as T-ends 82. When deploying multiple rings 80 in a stent structure, the T-ends will interlock to help hold the ring in place on the balloon or within the delivery tube. The interlock, however, does not provide a permanent attachment and, adjacent ring segments 80 will naturally release from each other during deployment. Moreover, since the interlocking structures are not actually attached, they permit a high degree of flexibility while the stent is being deployed. While T-ends are shown in FIG. 14, the terminal retainers could be L- or J-shaped ends or have any other geometry, which also provides for interlocking. In particular, each of these geometries will include a peripherally extending segment 83 which interlocks with a peripherally extending segment 83 on an adjacent T-end 82. Upon expansion of the ring 80, the segment 83 will move apart allowing the adjacent rings to deploy separately. When deploying multiple rings 80 in a stent structure, the T-, L- or J-ends will interlock to help hold the ring in place on the balloon or within the delivery tube. The interlock, however, does not provide a permanent attachment and, adjacent ring segments 80 will naturally release from each other during deployment. Such interlocking could also incorporated in the embodiments of FIGS. 5, 8, 11 and 12.

As illustrated thus far, the stent structures have generally maximized to vessel wall coverage achieved after expansion. While this will often be desired, in some instances it may be desired to lessen the amount of wall coverage. The stent structures shown in FIGS. 15A and 15B and FIGS. 16A and 16B, achieve such reduced wall coverage by providing "spacers" between adjacent rings.

Figure 15A:
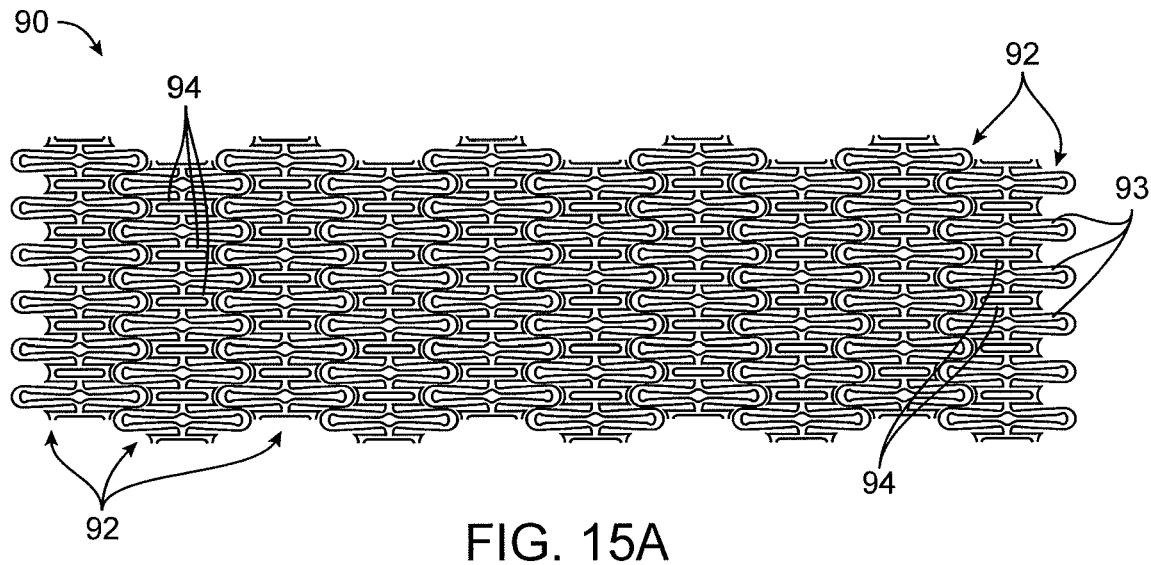
FIGS. 15A and 15B illustrate a further embodiment of a stent structure according to the present invention shown in unexpanded and expanded configurations, respectively.
Figure 15B:
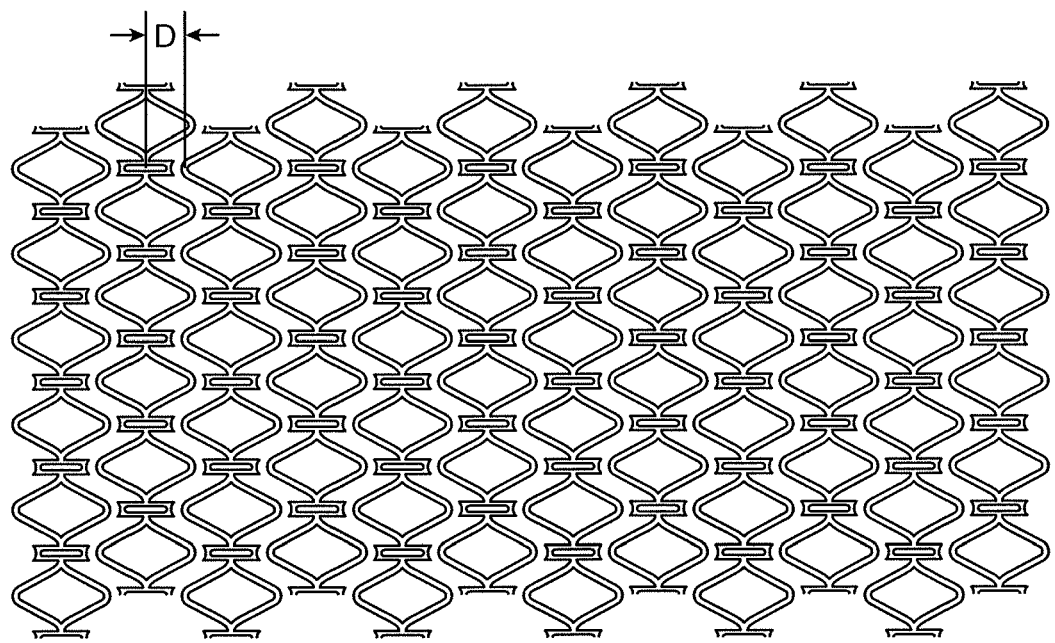
Figure 16A:
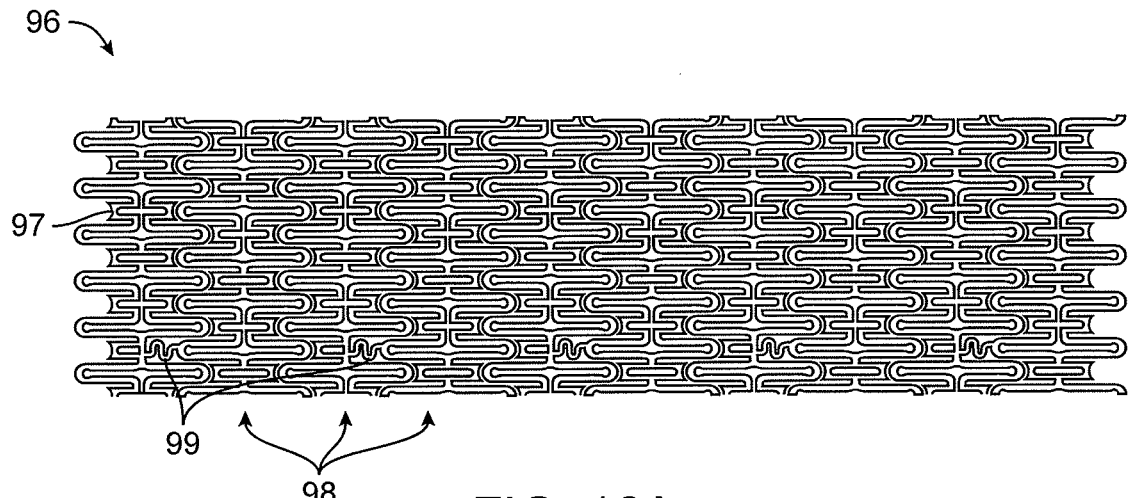
FIGS. 16A and 16B illustrate a still further embodiment of a stent structure according to the present invention shown in unexpanded and expanded configurations, respectively.
Figure 16B:
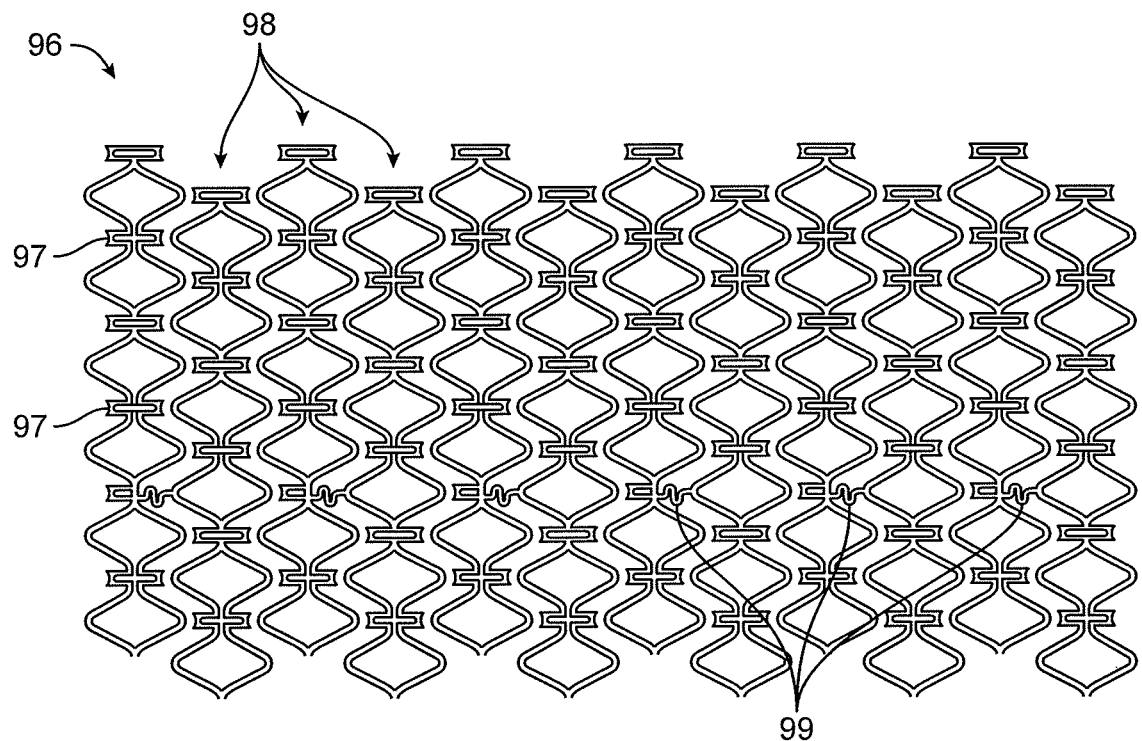

In FIG. 15A, a stent structure 90 includes independent rings 92 having boxes 93 circumferentially separated by spacers 94. The spacers 94 will either not expand or expand only after the boxes 93 have expanded, thus maintaining an axial distance D between adjacent rings after expansion, as shown in FIG. 15B. The distance D will be equal to about one-half the total axial length of the spacer 94.

Stent structure 96 (FIGS. 16A and 16B) is similar to structure 90, except that spaces 97 are axially split to define an H-shaped cell (as discussed with earlier embodiments) and certain of the rings 98 and joined by sigmoidal links 99.

Figure 17A:
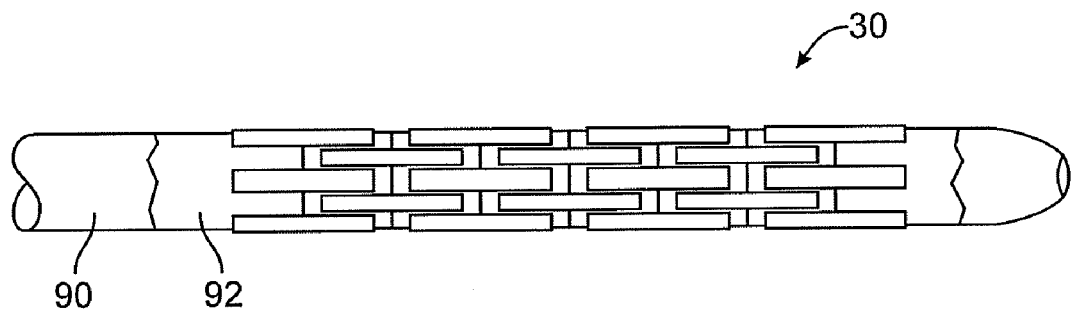
FIGS. 17A and 17C illustrate deployment of a closed cell stent structure according to the present invention with both a balloon having a single chamber (FIG. 16) and a balloon having multiple chambers to permit selective delivery of portions of the stent structure (FIG. 17).
Figure 17B:
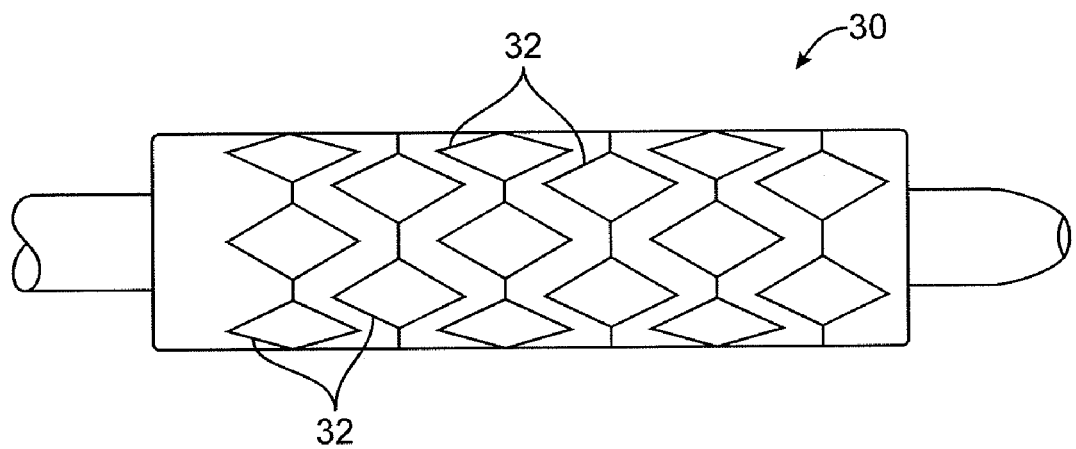
Figure 17C:
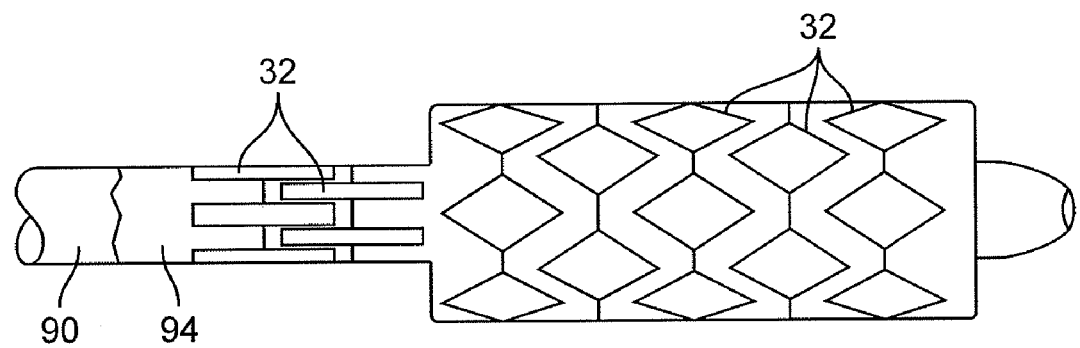

Stent structures according to the present invention may be delivered in a variety of ways. As illustrated in FIGS. 17A-17C, the stent structure 30 may be delivered on a balloon catheter 90 having a balloon 92 with a single inflation chamber. Deployment of the stent 30 is illustrated in FIG. 17B where all independent ring structures 32 are expanded simultaneously. Alternatively, as illustrated in FIG. 17C, catheter may carry a balloon 94 having a plurality of independently inflatable compartments. In that way, one or more of the independent compartments may be inflated separately from others of the compartments to selectively deploy one, two, three, or more of the independent ring structures 32. In that case, others of the ring structures 32 will remain unexpanded and available for separate expansion or may be simply removed from the patient if unused.

Figure 18D:
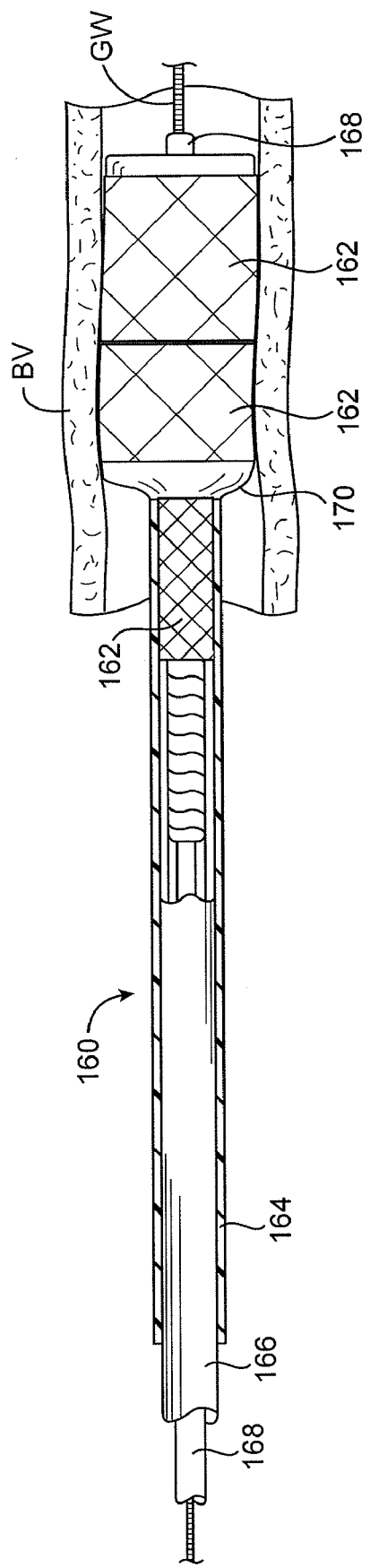
Figure 19:
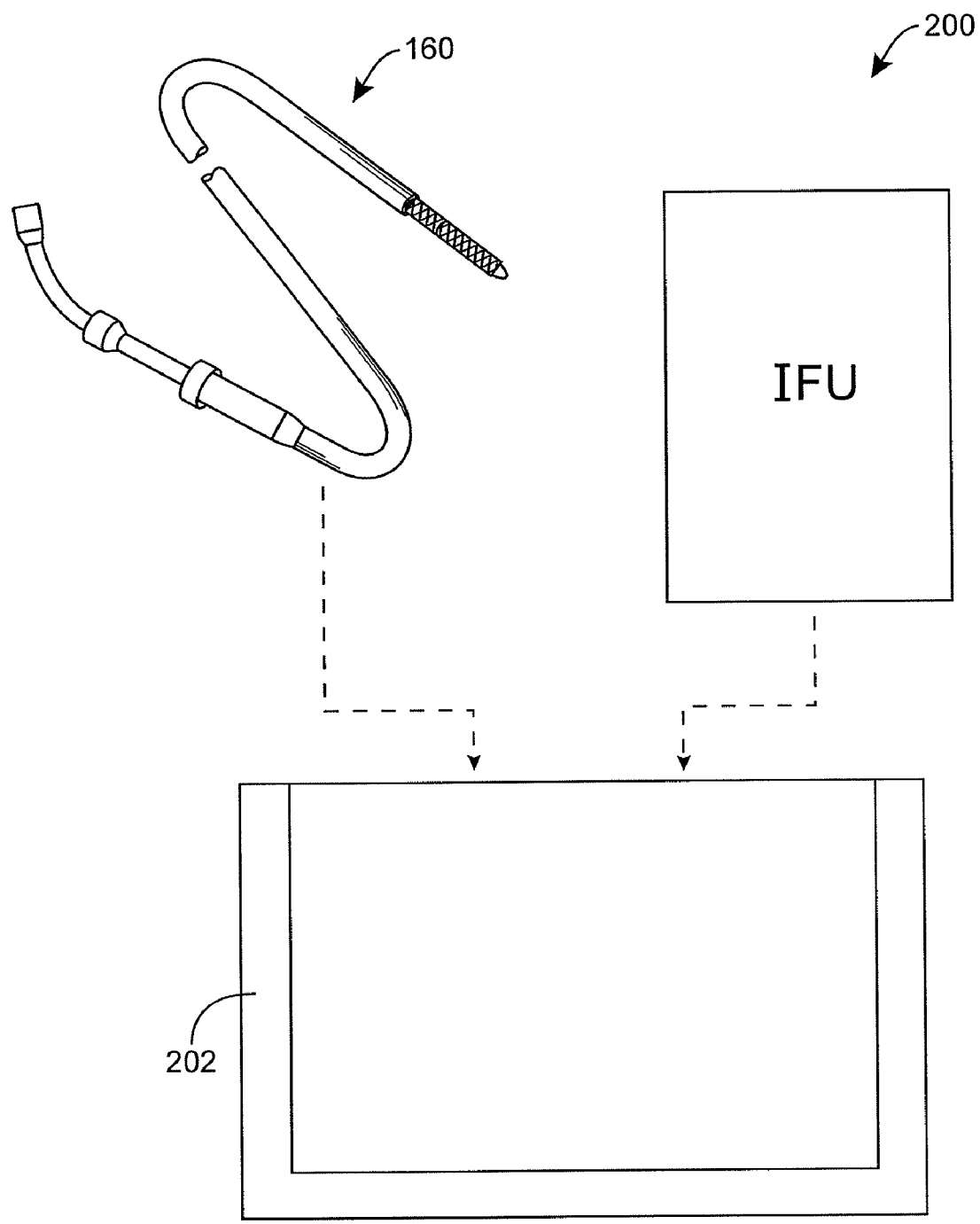
FIG. 19 illustrates a kit constructed in accordance with the principles of the present invention.

Referring now to FIGS. 18A-18D, an alternative stent structure delivery protocol employing a carrier tube will be described. Such delivery protocols are described in more detail in co-pending application Ser. No. 10/306,813, filed on Nov. 27, 2002, and in copending application Ser. No. 10/637, 713, filed Aug. 8, 2003, the full disclosures of which are incorporated herein by reference. Catheter 160 (FIG. 18A) comprises a sheath 164, pusher tube 166, and a catheter body 168. The catheter body 168 includes an expansible balloon 170 over its distal portion. Individual expansible rings, as described above, are deployed, as illustrated in FIGS. 18B and 18C, by first advancing the distal-most ring 162 using the pusher tube 166. The catheter body 168 is also distally advanced so that a distal portion of the balloon 170 lies within the distal-most deployed ring 162, as shown in FIG. 18B. The remaining proximal portion of the balloon 170 will, of course, remain within the other rings 162 which themselves remain within the sheath 164. The balloon 170 is then inflated, but only the advanced distal portion of the balloon inflates within the advanced ring 162, as illustrated in FIG. 18C. Expansion of the remaining proximal portion of the balloon is prevented by the sheath 164. Similarly, the remaining rings 162 remain unexpanded since they remain within the sheath 164.

Referring now to FIG. 18D, additional rings 162 may be deployed, either at the same target location within the blood vessel or at a different, spaced-apart locations within the blood vessel. Deployment of two rings 162 is illustrated. The two rings 162 are axially advanced using the pusher tube 162 so that they are positioned over the uninflated balloon 170. The balloon 170 is then inflated, as illustrated in FIG. 18D, thus expanding the rings 162 within the blood vessel BV. It will be appreciated that the catheter 160 could carry many more than the four illustrated rings 162, and three, four, five, ten, and even 20 or more individual rings could be deployed at one time, with additional single prostheses or groups of prostheses being deployed at different times and/or at different locations within the blood vessel. The use of "stent valves" as described in application Ser. No. 10/306,813, previously incorporated herein by reference, may preferably be employed to facilitate controlling the number of rings deployed and the spacing between the deployed and undeployed rings.

Referring now to FIG. 13, kits 200 according to the present invention comprise a catheter 160 (or a balloon catheter) in combination with instructions for use IFU. The instructions for use set forth any of the methods of the present invention, and in particular set forth how the catheter 160 may be used to implant a stent structure comprising multiple rings within a blood vessel or other body lumen. The catheter 160 and instructions for use will typically be packaged together, for example within a conventional package 202, such as a box, tube, pouch, tray, or the like. Catheter 160 will typically be maintained in a sterile condition within the package 202. The instructions for use may be provided on a package insert, may be printed in whole or in part on the packaging, or may be provided in other ways, such as electronically over the internet, on an electronic medium, such as a CD, DVD, or the like.

Figure 20A:
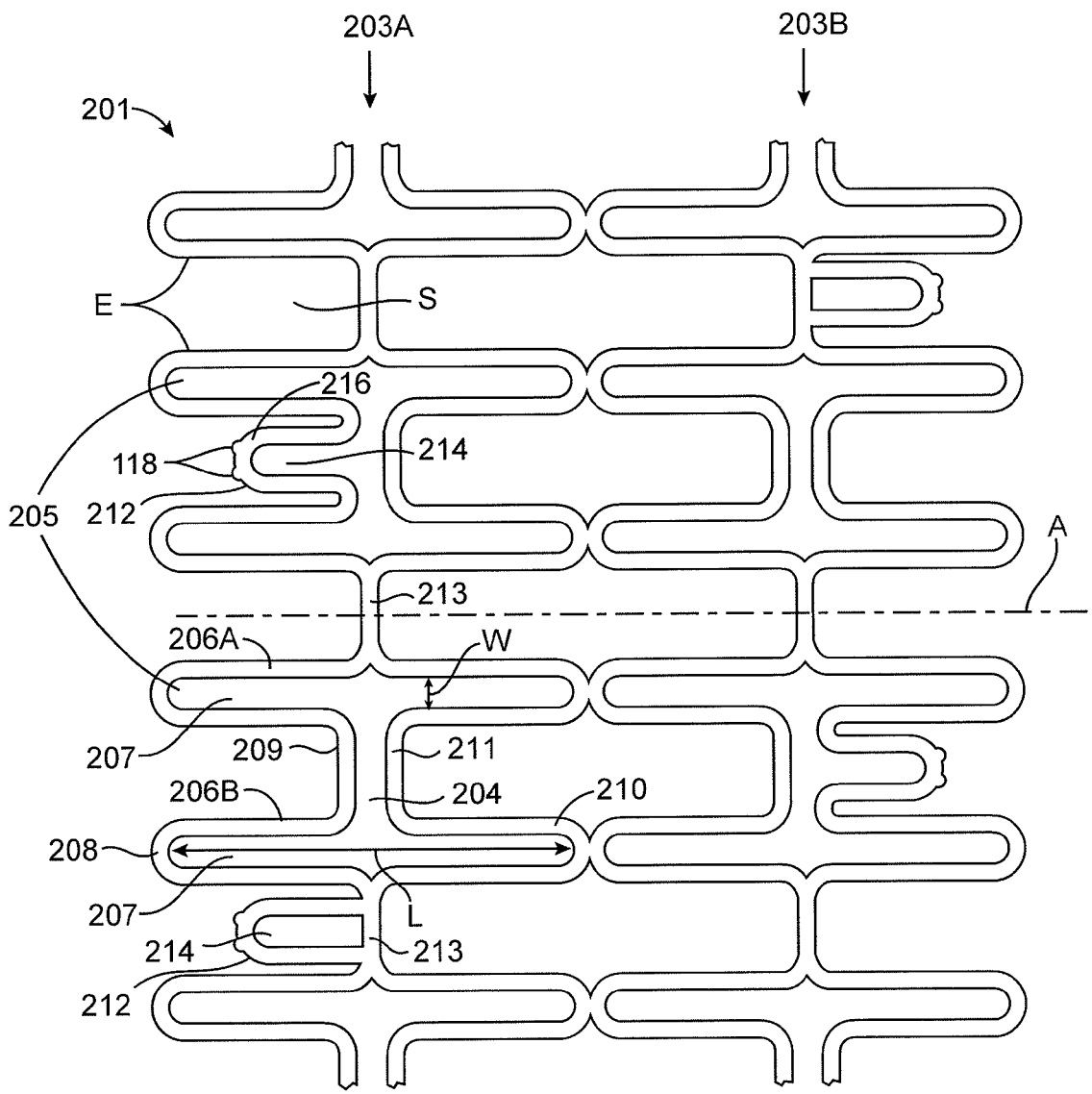
FIGS. 20A-20B, 21A-21B, and 22A-22B illustrate further embodiments of stent structures according to the invention in unexpanded and expanded configurations.
Figure 20B:
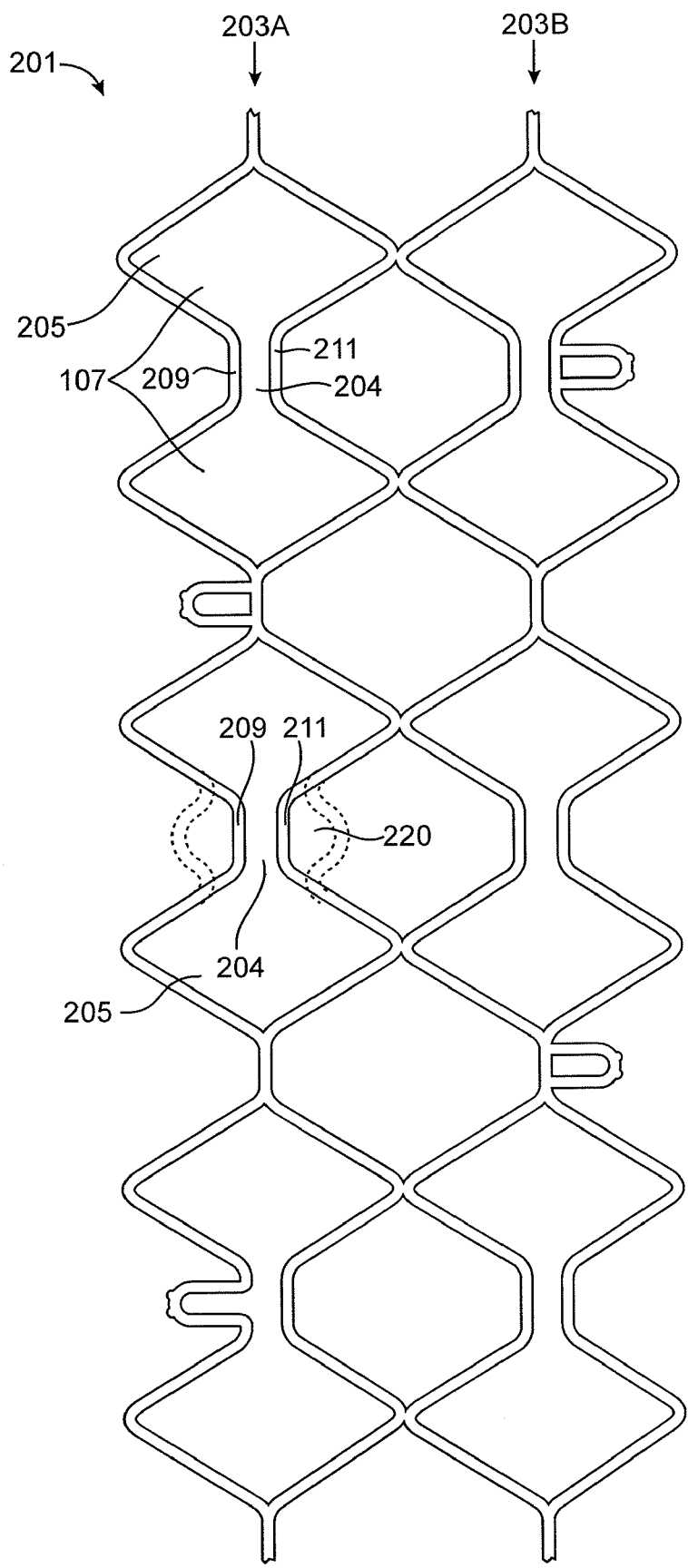

A further alternative stent structure according to the invention is illustrated in FIGS. 20A-20B. FIG. 20A illustrates a portion of a stent segment 201 in an unexpanded configuration, shown in a planar shape for clarity. Stent segment 201 comprises two parallel rows 203A, 203B of I-shaped cells 205 formed around an axis A so that stent segment 201 has a cylindrical shape. The terms "I-shaped" and "H-shaped" as used herein may refer to a similar cell geometry comprising two generally parallel slots connected by an interconnecting slot. Such cells may appear H-shaped when axis A is in a vertical orientation, or I-shaped axis A is in a horizontal orientation. Each cell 205 has upper and lower axial slots 207 aligned with the axial direction and a circumferential slot 204. Upper and lower slots 207 preferably have an oval, racetrack, rectangular or other oblong shape with a long dimension L generally parallel to axis A and a short dimension W perpendicular thereto. Axial slots 207 are bounded by upper axial struts 206A and lower axial struts 206B, curved outer ends 208 and curved inner ends 210. Each circumferential slot 204 is bounded by an outer circumferential strut 209 and an inner circumferential strut 211. Each I-shaped cell 205 is connected to the adjacent I-shaped cell 205 in the same row 98A or 98B by a circumferential connecting strut 213. All or a portion of cells 205 in row 98A merge or join with cells 205 in row 98B at the inner ends 210, which are integrally formed with the inner ends 210 of the adjacent cells 205.

Stent segment 201 is configured to interleave with an adjacent stent segment of similar construction. Upper and lower axial struts 206A, 206B and outer ends 208 form axial elements E that are received in the spaces S between each element E of the adjacent stent segment 201.

In a preferred embodiment, a spacing member 212 extends outwardly in the axial direction from a selected number of outer circumferential struts 209 and/or connecting struts 213. Spacing member 212 preferably itself forms a subcell 214 in its interior, but alternatively may be solid without any cell or opening therein. For those spacing members 212 attached to outer circumferential struts 209, subcell 214 preferably communicates with I-shaped cell 205. Spacing members 212 are configured to engage the curved outer ends 208 of an adjacent stent segment 201 so as to maintain appropriate spacing between adjacent stent segments. In one embodiment, spacing members 212 have outer ends 216 with two spaced-apart protrusions 218 that provide a cradle-like structure to index and stabilize the curved outer end 208 of the adjacent stent segment. Preferably, spacing members 212 have an axial length of at least about 10%, more preferably at least about 25%, of the long dimension L of I-shaped cells 205, so that the I-shaped cells 205 of adjacent stent segments are spaced apart at least that distance. This results in elements E interleaving a distance of at least about 10%, preferably at least about 25%, and more preferably at least about 50% of their axial length as measured from the circumferential connecting struts 213. Because spacing members 212 experience little or no axial shortening during expansion of stent segments 201, this minimum spacing between stent segments is maintained both in the unexpanded and expanded configurations.

FIG. 20B shows stent segment 201 of FIG. 20A in an expanded configuration. It may be seen that cells 205 are expanded so that upper and lower slots 207 are diamond shaped with circumferential slots 204 remaining basically unchanged. This results in some axial shortening of the stent segment, thereby increasing the spacing between adjacent stent segments. The stent geometry is optimized by balancing the amount of axial shortening and associated inter-segment spacing, the desired degree of vessel wall coverage, the desired metal density, and other factors. Because the stent is comprised of multiple unconnected stent segments 201, any desired number from 2 up to 10 or more stent segments may be deployed simultaneously to treat lesions of any length from 2 mm up to 100 mm or more. Further, because such segments are unconnected to each other, the deployed stent structure is highly flexible and capable of deployment in long lesions having curves and other complex shapes.

As an additional feature, circumferential slots 204 provide a pathway through which vessel side branches can be accessed for catheter interventions. Should stent segment 201 be deployed at a location in which it covers the ostium of a side branch to which access is desired, a balloon dilatation catheter may be positioned through circumferential slot 204 and expanded. This deforms circumferential struts 209, 211 axially outward, thereby expanding circumferential slot 204 and farther expanding upper and lower slots 207, as shown in phantom in FIG. 20B. This provides a relatively large opening 220 through which a catheter may be inserted through stent segment 201 and into the side branch for placing stents, performing angioplasty, or carrying out other interventions.

Figure 21A:
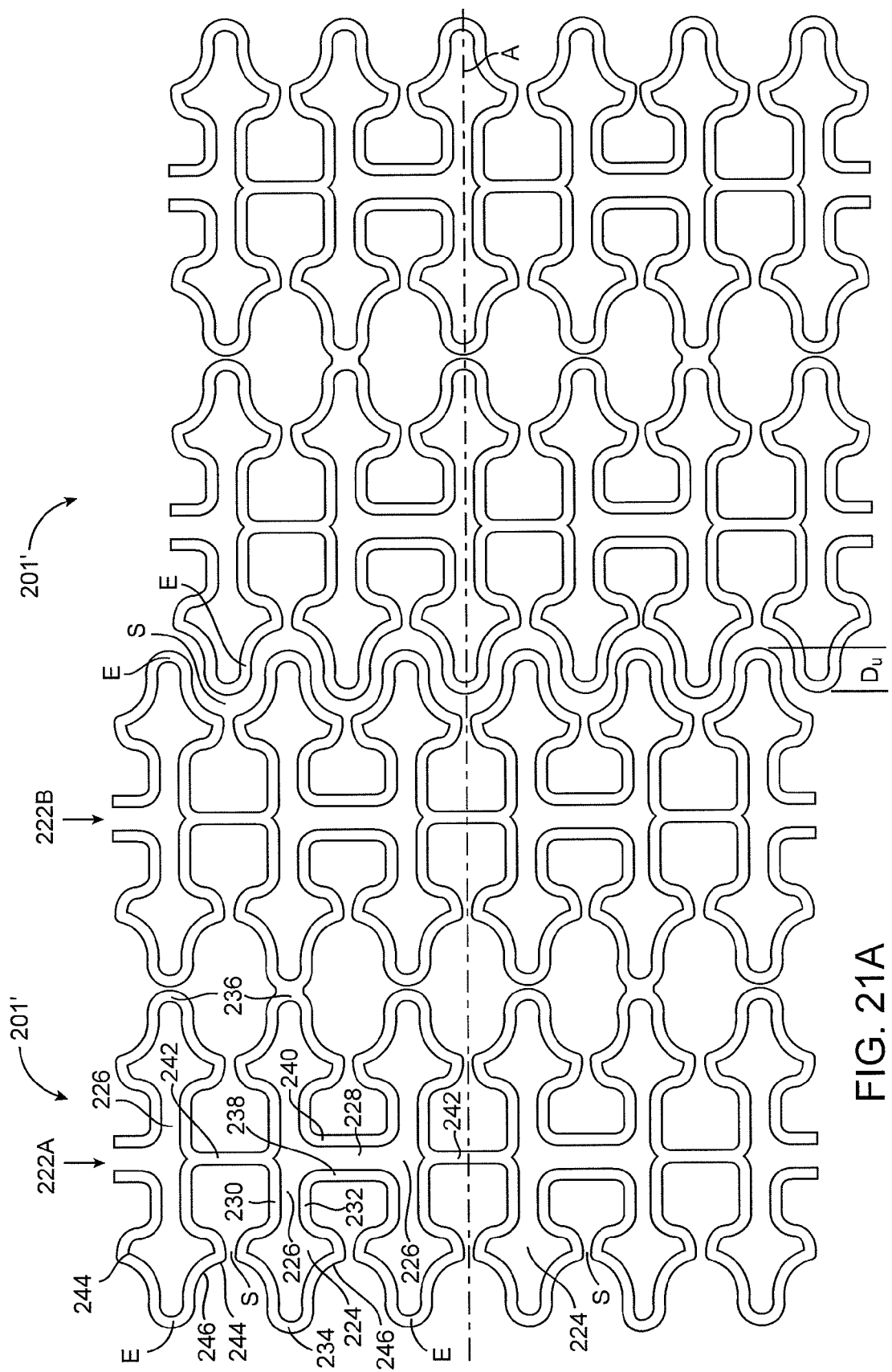
Figure 21B:
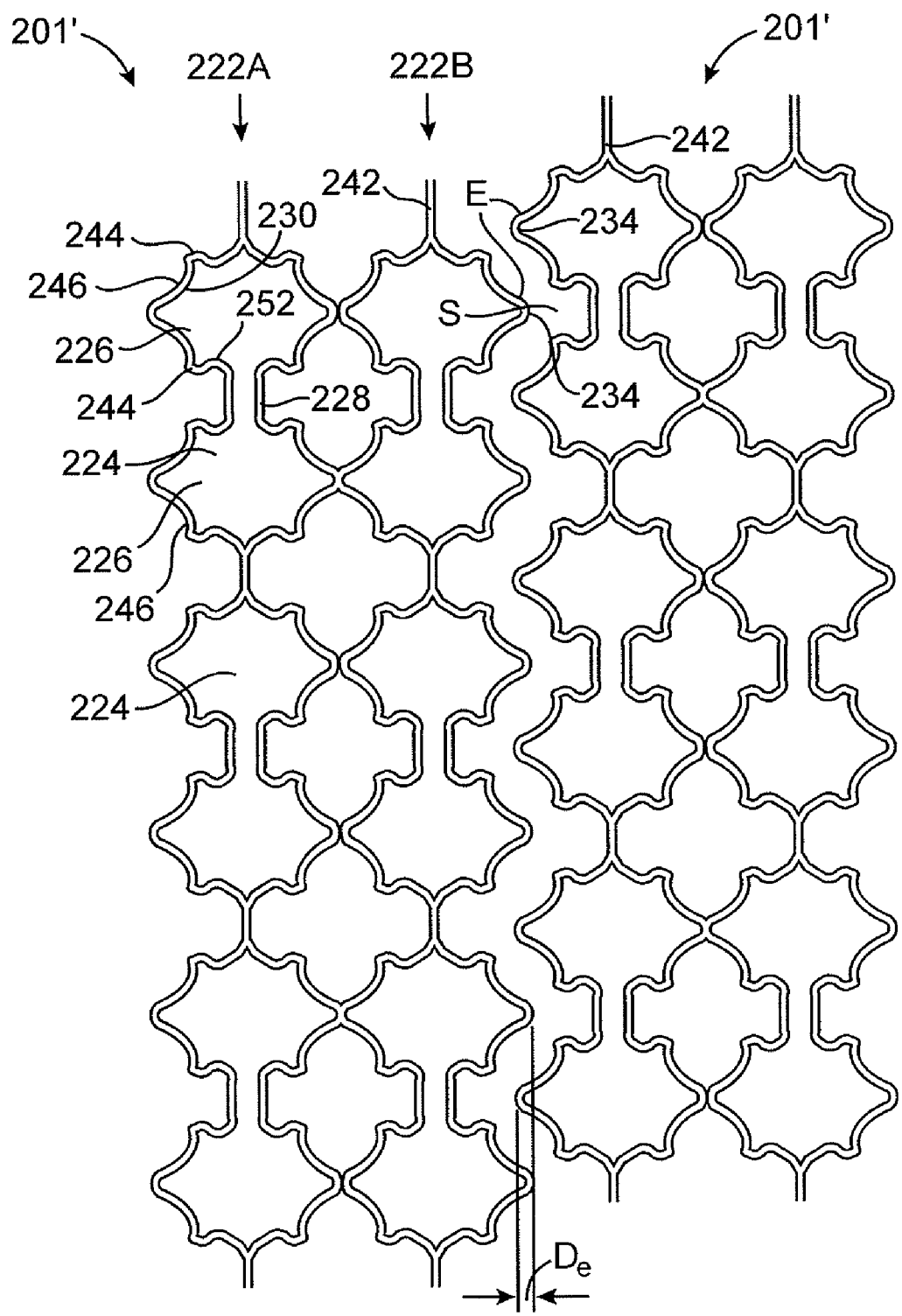

FIGS. 21A-21B illustrate a second embodiment of a stent segment 201' according to the invention. In FIG. 21A, two stent segments 201' are shown interleaved in a planar shape for clarity. Similar to the embodiment of FIG. 20A, stent segment 201' comprises two parallel rows 222A, 222B of I-shaped cells 224 formed into a cylindrical shape around axial axis A. Cells 224 have upper and lower axial slots 226 and a connecting circumferential slot 228. Upper and lower axial slots 226 are bounded by upper axial struts 230, lower axial struts 232, curved outer ends 234, and curved inner ends 236, forming axial elements E configured to be received in spaces S between elements E in the adjacent stent segment 201'. Circumferential slots 228 are bounded by an outer circumferential strut 238 and inner circumferential strut 240. Each I-shaped cell 224 is connected to the adjacent I-shaped cell 224 in the same row 222 by a circumferential connecting strut 242. Row 222A is connected to row 222B by the merger or joining of curved inner ends 236 of at least one and preferably two of slots 226 in each row 222.

One of the differences between the embodiment of FIGS. 21A-21B and that of FIGS. 20A-20B is the way in which spacing is maintained between the adjacent interleaved stent segments. In place of the spacing members 212 of the earlier embodiment, the embodiment of FIG. 21A includes a bulge 244 in upper and lower axial struts 230, 232 extending circumferentially outwardly from axial slots 226. These give axial slots 226 an arrowhead or cross shape at their inner and outer ends. The bulge 244 in each upper axial strut 230 extends toward the bulge 244 in a lower axial strut 232 in the same cell 205 or in an adjacent cell 205, thus narrowing the space S therebetween and creating a concave abutment 246 in the space between each axial slot 226. Concave abutments 246 are configured to receive and engage curved outer ends 234 of cells 224 in the adjacent stent segment, thereby maintaining spacing between the stent segments. The axial location of bulges 244 along upper and lower axial struts 230, 232 may be selected to provide the desired degree of inter-segment spacing. Preferably, the axial depth of concave abutments 246 from curved outer ends 234 is at least about 10% of the axial length of elements E (measured from circumferential struts 242), preferably at least about 25% of the axial length of elements E, and more preferably at least about 50% of the axial length of elements E.

FIG. 21B shows two stent segments 201 of FIG. 21A in an expanded condition. It may be seen that axial slots 226 are deformed into a circumferentially-widened modified diamond shape with bulges 244 on the now diagonal upper and lower axial struts 230, 232. Circumferential slots 228 are generally the same size and shape as in the unexpanded configuration. Bulges 244 have been pulled away from each other to some extent, but still provide a concave abutment 246 to maintain a minimum degree of spacing between adjacent stent segments. As in the earlier embodiment, some axial shortening of each segment occurs upon expansion and stent geometry can be optimized to provide the ideal intersegment spacing.

In a preferred embodiment, stent segments 201' retain some degree of interleaving in the expanded configuration, with outer ends 234 of elements E on adjacent stent segments being at least circumferentially aligned with each other, and preferably extending into spaces S of the adjacent stent segment a distance of at least about 1%, more preferably at least about 5%, and in some cases at least about 10% of the axial length of elements E as measured from circumferential connecting struts 242. In one exemplary embodiment, for a stent segment 201' having an axial length of 4 mm and an unexpanded diameter of about 0.5-1.5 mm, elements E have an axial length of about 1 mm and are interleaved a distance $D_u$ of about 0.1-0.5 mm in the unexpanded configuration. Segments 201' are expandable to a diameter of 2.5-3.5 mm and elements E are interleaved a distance $D_e$ of about 0.01-0.1 mm in the expanded configuration.

It should also be noted that the embodiment of FIGS. 21A-21B retains the feature described above with respect to FIGS. 20A-20B to enable access to vessel side branches blocked by stent segment 201'. Should such side branch access be desired, a dilatation catheter may be inserted into circumferential slot 228 and expanded to provide an enlarged opening through which a side branch may be entered.

Figure 22A:
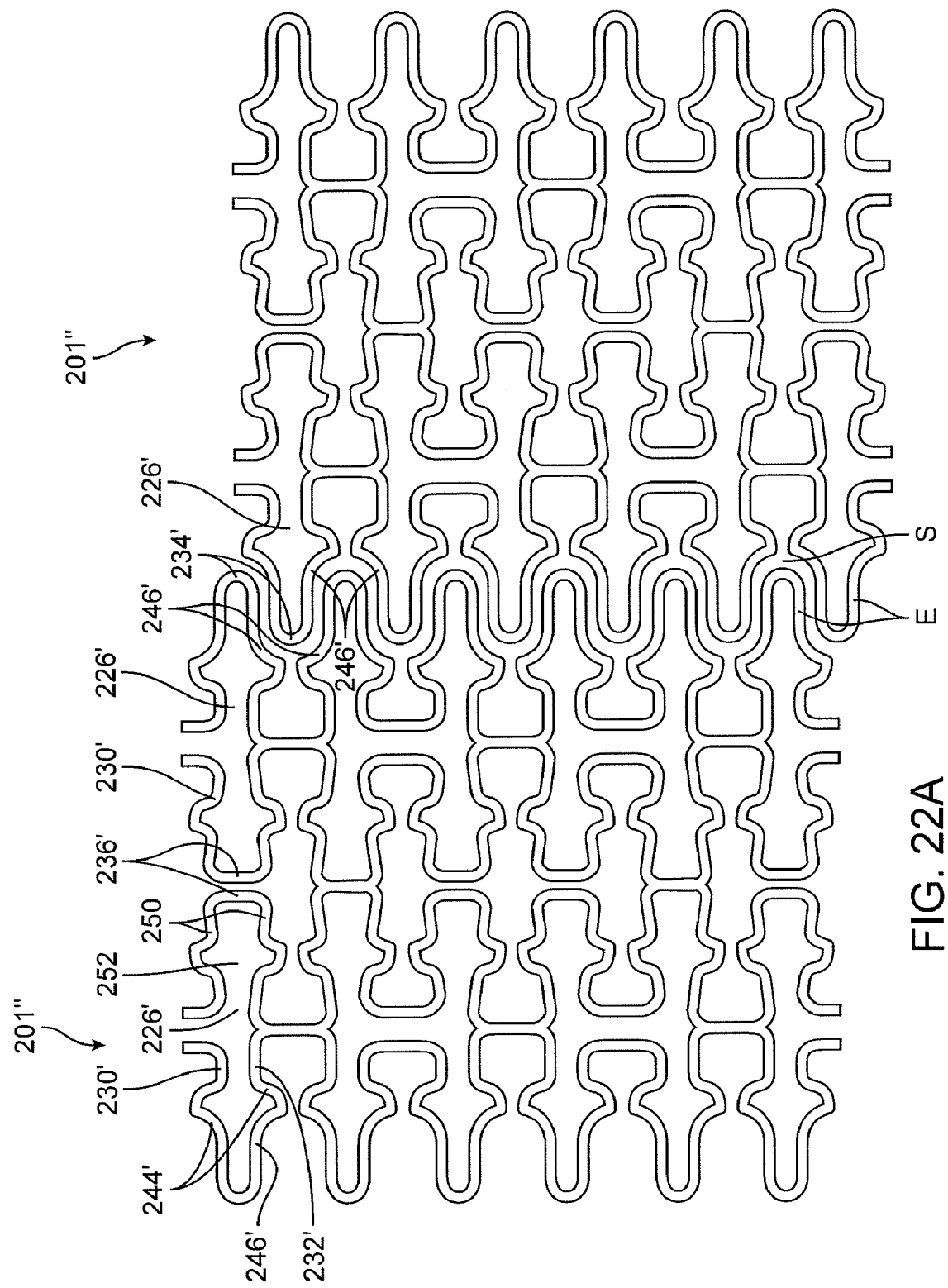
Figure 22B:
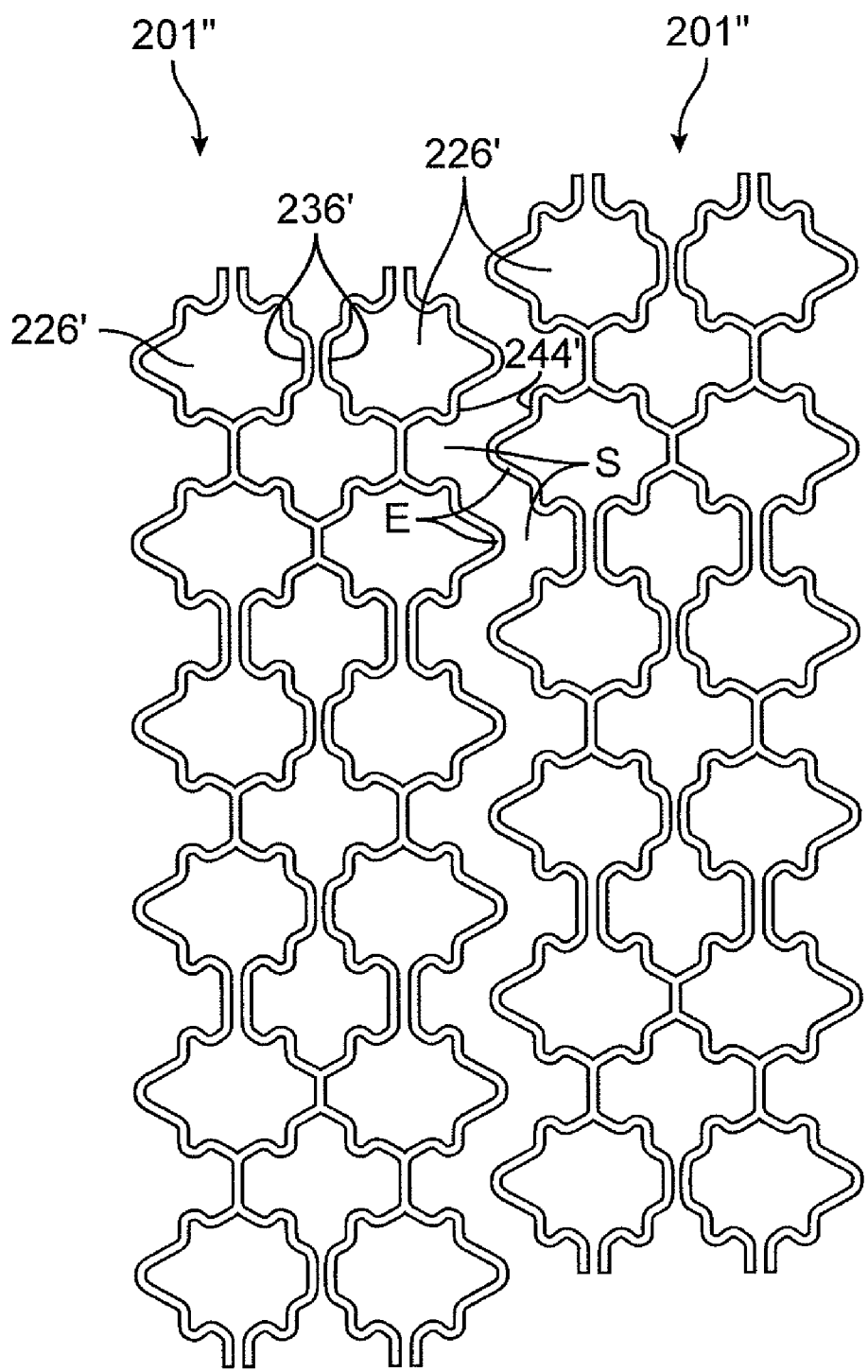

FIGS. 22A-22B illustrate a variant of the stent structure of FIGS. 21A-21B that has a larger expanded diameter. The primary difference in the embodiment of FIGS. 22A-22B is the geometry of the inner ends 236' of each axial slot 226'. Rather than being curved, inner ends 236' are generally straight and oriented in the circumferential direction. Because of the longer circumferential dimension of the inner ends 236', an inner portion 250 of each axial strut 230', 232' is disposed at an angle relative to the axial direction, giving the inner half 252 of each axial slot 226'a trapezoidal shape. Again, bulges 244' are disposed along axial struts 230', 232' so as to create concave abutments 246' that engage the outer ends 234' of axial slots 226' and maintain inter-segment spacing.

As shown in FIG. 22B, stent segment 201" expands to a configuration similar to that of FIG. 21B, with the exception that inner ends 236' remain generally straight and aligned with the circumferential direction. Axial slots 226' are again expanded into a modified diamond shape, with bulges 244' extending into spaces S to maintain inter-segment spacing. In an exemplary embodiment, stent segment 201" has a length of about 4 mm and diameter of about 1.0-2.0 mm when unexpanded, and is expandable to a diameter of about 3.0-4.0 mm.

The stent structures of the invention are preferably radiopaque so as to be visible by means of fluoroscopy. Radiopaque markers and/or materials may be used in or on the stent structures. Markers of radiopaque materials may be applied to the exterior of the stents, e.g, by applying a metal such as gold, platinum, a radiopaque polymer, or other suitable coating or mark on all or a portion of the stents. Alternatively, the stent structures may include a radiopaque cladding or coating or may be composed of radiopaque materials such as MP35N (ASTM 562), L-605 cobalt chromium (ASTM F90), other suitable alloys containing radiopaque elements, or multilayered materials having radiopaque layers. As a further option, the stent structures may have a geometry conducive to fluoroscopic visualization, such as having struts of greater thickness, sections of higher density, or overlapping struts. Some of the possible materials that may be used in the stent segments, either alone or in combination, include (by ASTM number):

F67-00 Unalloyed Titanium
F75-01 Cobalt-28 Chromium-6 Molybdenum Alloy
F90-01 Wrought Cobalt-20 Chromium-15 Tungsten-10 Nickel Alloy
F136-02a Wrought Titanium-6 Aluminum-4 Vanadium ELI Alloy
F138-00, F139-00 Wrought 18 Chromium-14 Nickel-2.5 Molybdenum Stainless Steel Bar or Sheet
F560-98 Unalloyed Tantalum
F562-02 Wrought 35 Cobalt-35 Nickel-20 Chromium-10 Molybdenum Alloy
F563-00 Wrought Cobalt-20 Nickel-20 Chromium 3.5 Molybdenum-3.5 Tungste-5 Iron Alloy F688 Wrought Cobalt-35 Nickel-20 Chromium-10 Molybdenum Alloy
F745-00 18 Chromium-12.5 Nickel-2.5 Molybdenum Stainless Steel
F799-02 Cobalt-28 Chromium-6 Molybdenum Alloy
F961-96 Cobalt-35 Nickel-20 Chromium-10 Molybdenum Alloy
F1058-02 Wrought 40 Cobalt-20 Chromium-16 Iron-15 Nickel-7 Molybdenum Alloy
F1091-02 Wrought Cobalt-20 Chromium-15 Tungsten-10 Nickel Alloy
F1108 Titanium-6 Aluminum-4 Vanadium Alloy
F1295-01 Wrought Titanium-6 Aluminum-7 Niobium Alloy
F1314-01 Wrought Nitrogen-strengthened 22 Chromium-13 Nickel-5 Manganese-2.5 Molybdenum Stainless Steel Alloy
F1241-99 Unalloyed Titanium Wire
F1350-02 Wrought 18 Chromium-14 Nickel-2.5 Molybdenum Stainless Steel Wire
F1377-98a Cobalt-28 Chromium-6 Molybdenum Powder coating
F1472-02a Wrought Titanium-6 Aluminum-4 Vanadium Alloy
F1537-00 Wrought Cobalt-28 Chromium-6 Molybdenum Alloy
F1580-01 Titanium and Titanium-6 Aluminum-4 Vanadium Alloy Powder coating
F1586-02 Wrought Nitrogen Strengthened 21 Chromium-10 Nickel-3 Manganese-2.5 Molybdenum Stainless Steel Bar
F1713-96 Wrought Titanium-13 Niobium-13 Zirconium Alloy
F1813-01 Wrought Titanium-12 Molybdenum-6 Zirconium-2 Iron Alloy
F2063-00 Wrought Nickel-Titanium Shape Memory Alloys
F2066-01 Wrought Titanium-15 Molybdenum Alloy
F2146-01 Wrought Titanium-3 Aluminum-2.5 Vanadium Alloy Seamless Tubing
F2181-02a Wrought Stainless Steel Tubing The preferred embodiments of the invention are described above in detail for the purpose of setting forth a complete disclosure and for the sake of explanation and clarity. Those skilled in the art will envision other modifications within the scope and sprit of the present disclosure.

What is claimed is:

1. A stent structure comprising:
a plurality of radially expansible closed cell rings arranged along an axial line, each of the rings having an unexpanded crimped configuration suitable for mounting on a delivery catheter for delivery into a blood vessel and an expanded configuration in which an expanded ring engages a wall of the vessel, wherein at least some of the axially adjacent rings are separable from an adjacent ring and wherein at least some of the axially separable rings comprise axially extending closed cell structures which, when the radially expansible closed cell rings are in the unexpanded crimped configuration, interleave with axially extending closed cell structures on an adjacent separable ring, without interlocking with the adjacent separable ring, none of the axially extending closed cell structures constraining axial separation of the adjacent rings in the unexpanded crimped configuration, and wherein the axially extending closed cell structures widen as the rings are expanded and wherein at least some of the axially separable rings further comprise spacers which engage the axially extending closed cell structures on adjacent rings to provide a preselected spacing between adjacent rings upon radial expansion, wherein the spacer comprises an axially extending strut having an axial extension length, the axially extending strut disposed between two adjacent axially extending closed cell structures on the same ring, the two adjacent axially extending closed cell structures having an axial length greater than the axial extension length of the strut.

2. A stent structure as in claim 1, wherein the axially extending closed cell structures are selected from the group consisting of boxes, diamonds, rhomboids, ovals, and ellipses.

3. A stent structure as in claim 1, wherein the axially extending closed cell structures are defined by a slot pattern selected from the group consisting of I-patterns, H-patterns, and J-patterns.

4. A stent structure as in claim 1, wherein the axially separable rings are configured to axially shorten upon expansion.

5. A stent structure as in claim 1, wherein the axially extending closed cell structures remain interleaved following expansion.

6. A stent structure as in claim 1, wherein the axially extending closed cell structures axially interleave over a distance of at least 0.1 mm prior to stent expansion.

7. A stent structure as in claim 6, wherein the distance is in the range from 1 mm to 5 mm.

8. A stent structure as in claim 1, wherein the rings have axial lengths in range from 1 mm to 10 mm, prior to radial expansion.

9. A stent structure as in claim 1, consisting of from two to 50 expansible ring structures.

10. A stent structure as in claim 1, wherein the radially expansible rings releasably carry a biologically active agent.

11. A stent structure as in claim 10, wherein the biologically active agent inhibits hyperplasia.

12. A stent structure as in claim 11, wherein the biologically active agent is selected from the group consisting of anti-neoplastic drugs, including paclitaxel, methotrexate, and batimastal; antibiotics including doxycycline, tetracycline, rapamycin, and actinomycin; immunosuppressants including dexamethasone, and methyl prednisolone; nitric oxide sources including nitroprussides; estrogen; and estradiols.

13. A stent structure as in claim 1, wherein the spacers expand only after the expansible closed structures have widened.

14. A stent structure as in claim 1, wherein the spacers do not expand upon radial expansion of the radially expansible rings.

15. A stent structure as in claim 1, wherein each of the axially extending closed cell structures of the rings are coupled by a spacer.

16. A stent structure as in claim 1, wherein each of the plurality of radially expansible closed cell rings are symmetrical about a centerline, and wherein the spacers extend from the centerline.

17. A stent structure as in claim 16, wherein the spacers are symmetrical about the centerline.

18. A stent deployment system comprising:
an elongated carrier having a central axis;
a plurality of radially expansible closed cell rings expandable into an expanded configuration in which an expanded ring engages a blood vessel wall, the rings arranged over a surface of the elongated carrier in an unexpanded crimped configuration suitable for delivery into the blood vessel, wherein at least some of the radially expansible closed cell rings are separable from an adjacent ring and comprise axially extending closed cell structures which, when the rings are in the unexpanded crimped configuration, interleave with axially extending closed cell structures on an adjacent unconnected ring without interlocking with the adjacent radially expansible ring, none of the axially extending closed cell structures constraining axial separation of the adjacent rings in the unexpanded crimped configuration, and wherein the axially extending closed cell structures widen as the rings are expanded and wherein at least some of the axially separable rings further comprise spacers which engage the axially extending closed cell structures on adjacent rings to provide a preselected spacing between adjacent rings upon radial expansion, wherein the spacer comprises an axially extending strut having an axial extension length, the axially extending strut disposed between two adjacent axially extending closed cell structures on the same ring, the two adjacent axially extending closed cell structures having an axial length greater than the axial extension length of the strut.

19. A stent deployment system as in claim 18, wherein the stent deployment system comprises a balloon having a plurality of independent chambers wherein individual expansible rings are disposed over single independently inflatable chambers.

20. A stent deployment system as in claim 19, wherein the rings are axially slidable over the outer surface of the balloon.

21. A stent deployment system as in claim 18, wherein the elongated carrier comprises a carrier tube having an inner surface which constrains the radially expansible rings.

22. A stent deployment system as in claim 21, further comprising a pusher tube arranged to axially advance the radially expansible rings from the carrier tube.

23. A stent deployment system as in claim 22, wherein the radially expansible rings are resilient and radially constrained so that they expand when advanced distally from the carrier tube.

24. A stent deployment system as in claim 18, wherein the radially expansible rings are deformable, said structure further comprising a balloon arranged to expand individual rings as said rings are advanced from the carrier tube.

25. A stent deployment system as in claim 18, wherein the axially extending closed cell structures are selected from the group consisting of boxes, rhomboids, ovals, ellipses, diamonds, and irregular polygons.

26. A stent deployment system as in claim 18, wherein the axially extending closed cell structures are defined by a slot pattern selected from the group consisting of I-patterns and H-patterns.

27. A stent deployment structure as in claim 18, wherein the radially expansible rings are configured to axially shorten upon expansion.

28. A stent deployment structure as in claim 18, wherein the axially extending closed cell structures remain interleaved following expansion.

29. A stent deployment structure as in claim 18, wherein the axially extending closed cell structures axially interleave over a distance of at least 0.1 mm prior to stent expansion.

30. A stent deployment structure as in claim 29, wherein the distance is in the range from 1 mm to 5 mm.

31. A stent deployment system as in claim 18, wherein the rings have axial lengths in range from 1 mm to 10 mm, prior to radial expansion.

32. A stent deployment system as in claim 31, consisting of from two to 50 expansible ring structures.

33. A stent deployment system as in claim 18, wherein the radially expansible rings releasably carry a biologically active agent.

34. A stent deployment system as in claim 33, wherein the biologically active agent inhibits hyperplasia.

35. A stent deployment system as in claim 34, wherein the biologically active agent is selected from the group consisting of anti-neoplastic drugs including paclitaxel, methotrexate, and batimastal; antibiotics including doxycycline, tetracycline, rapamycin, and actinomycin; immunosuppressants including dexamethasone and methyl prednisolone; nitric oxide sources including nitroprussides; estrogen; and estradiols.

36. A stent deployment system as in claim 18, wherein the elongated carrier is adapted to axially separate the adjacent unconnected rings in the unexpanded configuration.

37. A stent deployment system as in claim 36, wherein the elongated carrier comprises a valve member adapted to engage at least one ring to separate the at least one ring from an adjacent unconnected ring.

38. A stent deployment system as in claim 18, wherein the axially extending closed cell structures have an overlapping portion which is received between axially extending closed cell structures of an adjacent ring, the overlapping portion comprising a pair of axial struts separated by a circumferential distance which is constant or tapering toward the adjacent ring throughout all of the overlapping portion.

39. A stent deployment system as in claim 38, wherein adjacent axially extending closed cell structures form a concave region therebetween having a closed end, the spacers maintaining a gap between the closed end and an axially extending closed cell structure of the adjacent ring.

40. A stent deployment system as in claim 39, wherein the spacer comprises a cradle structure adapted to receive an axially extending closed cell structure on an adjacent ring.

41. A stent deployment system as in claim 39, wherein the spacer comprises a concave abutment.

42. A stent structure as in claim 18, wherein the spacers expand only after the expansible closed structures have widened.

43. A stent structure as in claim 18, wherein the spacers do not expand upon radial expansion of the radially expansible rings.

44. A stent structure comprising:
a plurality of radially expansible closed cell rings arranged along an axial line and uncovered by material extending between adjacent rings, each of the rings having an unexpanded crimped configuration suitable for mounting on a delivery catheter for delivery into a blood vessel and an expanded configuration in which an expanded ring engages a wall of the vessel, wherein at least some of the axially adjacent rings are separable from an adjacent ring and wherein at least some of the axially separable rings comprise axially extending closed cell structures which, when the radially expansible closed cell rings are in the unexpanded crimped configuration, interleave with axially extending closed cell structures on an adjacent separable ring without interlocking with the adjacent separable ring, none of the axially extending closed cell structures constraining axial separation of the adjacent rings in the unexpanded crimped configuration, thereby allowing each of the separable rings to be expanded without expanding an adjacent unconnected ring and wherein at least some of the axially separable rings further comprise spacers which engage the axially extending closed cell structures on adjacent rings to provide a preselected spacing between adjacent rings upon radial expansion, wherein the spacer comprises an axially extending strut having an axial extension length, the axially extending strut disposed between two adjacent axially extending closed cell structures on the same ring, the two adjacent axially extending closed cell structures having an axial length greater than the axial extension length of the strut.

45. A stent structure as in claim 44, wherein at least some of the axially extending closed cell structures widen as the rings are expanded.

46. A stent structure as in claim 45, wherein the axially extending closed cell structures are selected from the group consisting of boxes, diamonds, rhomboids, ovals, and ellipses.

47. A stent structure as in claim 45, wherein the axially extending closed cell structures are defined by a slot pattern selected from the group consisting of I-patterns, H-patterns, and J-patterns.

48. A stent structure as in claim 44, wherein the axially separable rings are configured to axially shorten upon expansion.

49. A stent structure as in claim 44, wherein the axially extending closed cell structures remain interleaved following expansion.

50. A stent structure as in claim 44, wherein the axially extending closed cell structures axially interleave over a distance of at least 0.1 mm prior to stent expansion.

51. A stent structure as in claim 50, wherein the distance is in the range from 1 mm to 5 mm.

52. A stent structure as in claim 44, wherein the rings have axial lengths in range from 1 mm to 10 mm, prior to radial expansion.

53. A stent structure as in claim 44, consisting of from two to 50 expansible ring structures.

54. A stent structure as in claim 44, wherein the radially expansible rings releasably carry a biologically active agent.

55. A stent structure as in claim 54, wherein the biologically active agent inhibits hyperplasia.

56. A stent structure as in claim 55, wherein the biologically active agent is selected from the group consisting of anti-neoplastic drugs, including paclitaxel, methotrexate, and batimastal; antibiotics including doxycycline, tetracycline, rapamycin, and actinomycin; immunosuppressants including dexamethasone, and methyl prednisolone; nitric oxide sources including nitroprussides; estrogen; and estradiols.

57. A stent structure as in claim 1, wherein the axially extending closed cell structures have an overlapping portion which is received between axially extending closed cell structures of an adjacent ring, the overlapping portion comprising a pair of axial struts separated by a circumferential distance which is constant or tapering toward the adjacent ring throughout all of the overlapping portion.

58. A stent structure as in claim 57, wherein adjacent axially extending closed cell structures form a concave region therebetween having a closed end, the spacers maintaining a gap between the closed end and an axially extending closed cell structure of the adjacent ring.

59. A stent structure as in claim 58, wherein the spacer comprises a cradle structure adapted to receive an axially extending closed cell structure on an adjacent ring.

60. A stent structure as in claim 58, wherein the spacer comprises a concave abutment.

61. A stent structure as in claim 44, wherein the axially extending closed cell structures have an overlapping portion which is received between axially extending closed cell structures of an adjacent ring, the overlapping portion comprising a pair of axial struts separated by a circumferential distance which is constant or tapering toward the adjacent ring throughout all of the overlapping portion.

62. A stent structure as in claim 61, wherein adjacent axially extending closed cell structures form a concave region therebetween having a closed end, the spacers maintaining a gap between the closed end and an axially extending closed cell structure of the adjacent ring.

63. A stent structure as in claim 62, wherein the spacer comprises a cradle structure adapted to receive an axially extending closed cell structure on an adjacent ring.

64. A stent structure as in claim 62, wherein the spacer comprises a concave abutment.

65. A stent structure as in claim 44, wherein the spacers expand only after the expansible closed structures have widened.

66. A stent structure as in claim 44, wherein the spacers do not expand upon radial expansion of the radially expansible rings.

* * * * *